US010946126B2

(12) United States Patent
Taylor et al.

(10) Patent No.: US 10,946,126 B2
(45) Date of Patent: Mar. 16, 2021

(54) ELECTROCARDIOGRAPHY TRIGGERED PISTON PUMP

(71) Applicant: University of Louisiana at Lafayette, Lafayette, LA (US)

(72) Inventors: Charles Taylor, Lafayette, LA (US); Jacob King, Carencro, LA (US)

(73) Assignee: University of Louisiana at Lafayette, Lafayette, LA (US)

(*) Notice: Subject to any disclaimer, the term of this patent is extended or adjusted under 35 U.S.C. 154(b) by 133 days.

(21) Appl. No.: 16/151,786

(22) Filed: Oct. 4, 2018

(65) Prior Publication Data
US 2019/0117863 A1    Apr. 25, 2019

Related U.S. Application Data

(60) Provisional application No. 62/567,916, filed on Oct. 4, 2017.

(51) Int. Cl.
*A61M 1/10* (2006.01)

(52) U.S. Cl.
CPC ............ *A61M 1/1086* (2013.01); *A61M 1/10* (2013.01); *A61M 1/1008* (2014.02); *A61M 1/1029* (2014.02); *A61M 1/1096* (2014.02); *A61M 2205/3606* (2013.01); *A61M 2205/366* (2013.01); *A61M 2230/06* (2013.01)

(58) Field of Classification Search
CPC .... A61M 1/1086; A61M 1/10; A61M 1/1096; A61M 1/1008; A61M 1/1029; A61M 2205/3606; A61M 2230/06; A61M 2205/36
See application file for complete search history.

(56) References Cited

U.S. PATENT DOCUMENTS

| 2003/0072679 A1* | 4/2003 | Johnson | ................ B01L 3/0265 506/33 |
| 2005/0063860 A1* | 3/2005 | Carpenter | ........... A61M 1/1698 422/45 |
| 2006/0122552 A1* | 6/2006 | O'Mahony | ........... A61M 1/342 604/6.11 |

(Continued)

*Primary Examiner* — Catherine M Voorhees
(74) *Attorney, Agent, or Firm* — Russel O. Primeaux; Jessica C. Engler; Kean Miller LLP

(57) ABSTRACT

A positive displacement pump that triggers with the beating of a mammalian heart, through the monitoring of an ECG signal is disclosed. A programmable delay from the detection of the forthcoming contraction of the heart enables the pump to syncopate the ejection of the fluid with the events occurring in the cardiovascular system. This delayed ejection could be used to overlay the ejected fluid from the pump with a pressure wave in the artery of systemic circulation through a catheter connection between the pump and a physiological model (e.g., cow, dog, human). The outcome of this use could be to raise the pulse pressure in the system to take advantage of physiological pathways that respond to this transient change in blood pressure. The novelty of this system stems from the adaptable control architecture designed to augment the pulsatile characteristics of the cardiovascular system. This inventive concept could be expanded to encompass the augmentation (dampen or enhance) of pulsatile characteristics in any oscillating flow system.

4 Claims, 41 Drawing Sheets

(56) References Cited

U.S. PATENT DOCUMENTS

| | | | |
|---|---|---|---|
| 2008/0031773 A1* | 2/2008 | Eccleston | A61M 1/3666 |
| | | | 422/44 |
| 2008/0156476 A1* | 7/2008 | Smisson | A61M 5/44 |
| | | | 165/185 |
| 2008/0294096 A1* | 11/2008 | Uber, III | A61M 31/005 |
| | | | 604/66 |
| 2009/0069787 A1* | 3/2009 | Estes | G16H 20/17 |
| | | | 604/503 |
| 2009/0099498 A1* | 4/2009 | Demers | A61M 1/106 |
| | | | 604/6.09 |
| 2013/0102849 A1* | 4/2013 | Criscione | A61F 2/2481 |
| | | | 600/204 |
| 2014/0299544 A1* | 10/2014 | Wilt | A61M 1/1601 |
| | | | 210/646 |
| 2016/0213827 A1* | 7/2016 | Tanner | A61M 1/122 |
| 2018/0207397 A1* | 7/2018 | Look | A61M 1/0084 |

* cited by examiner

| | Cycle Period | Ratio of Fills: Eject | Ejection Volume | Delay |
|---|---|---|---|---|
| Cycle Period [sec] | Varied | 0.35 | 0.35 | 0.35 |
| Percent Systole [%] | 30 | 30 | 30 | 30 |
| Peak Flow Rate Ejection [lpm] | 19.30 | 19.30 | Varied | 19.30 |
| Fill: Eject Ratio | 1:1 | Varied | 1:1 | 1:1 |
| Triggering Delay [ms] | 18.55 | 18.55 | 18.55 | Varied |
| Peak Flow Rate Fill [lpm] | 14 | 14 | 14 | 14 |

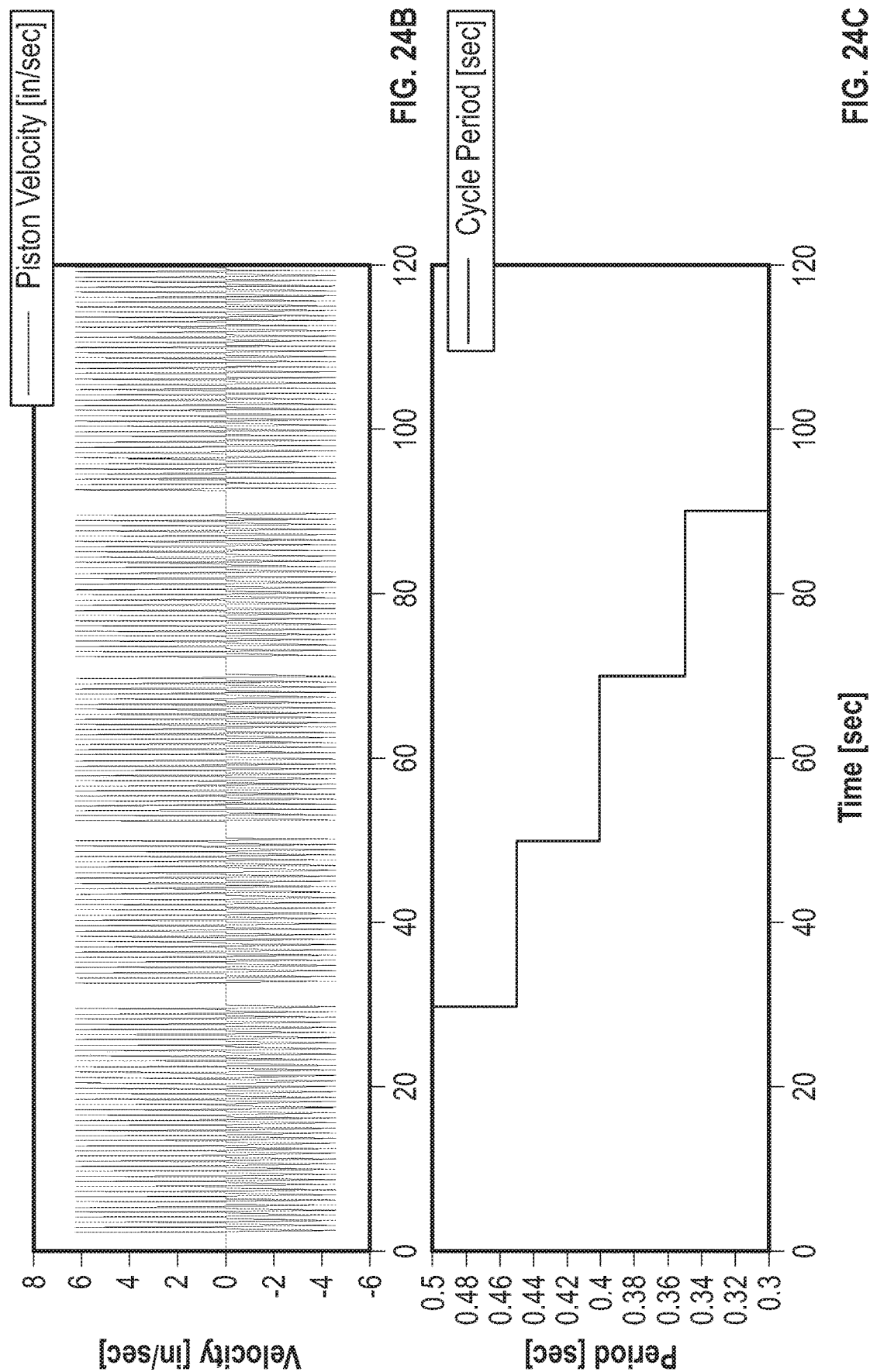

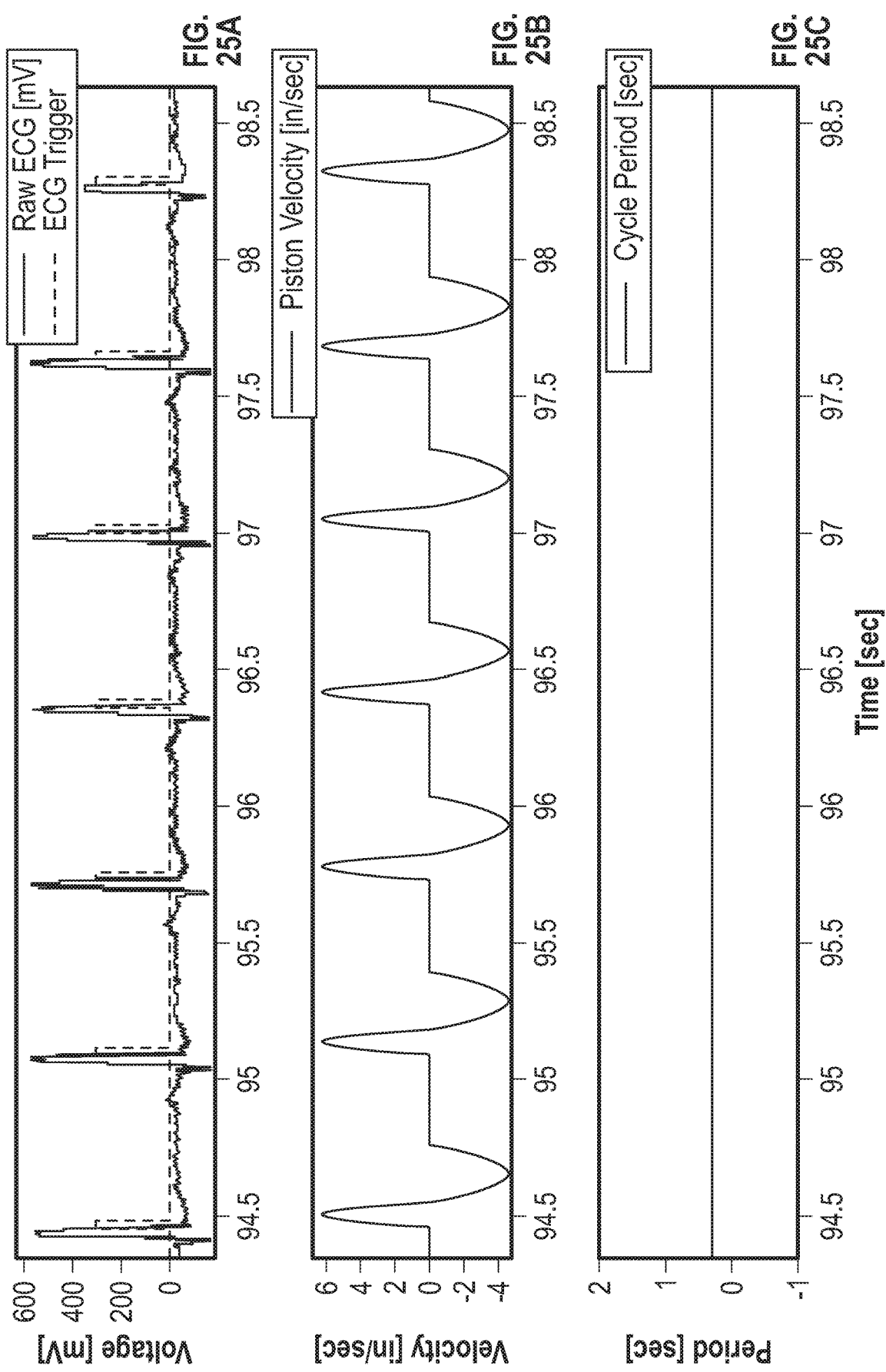

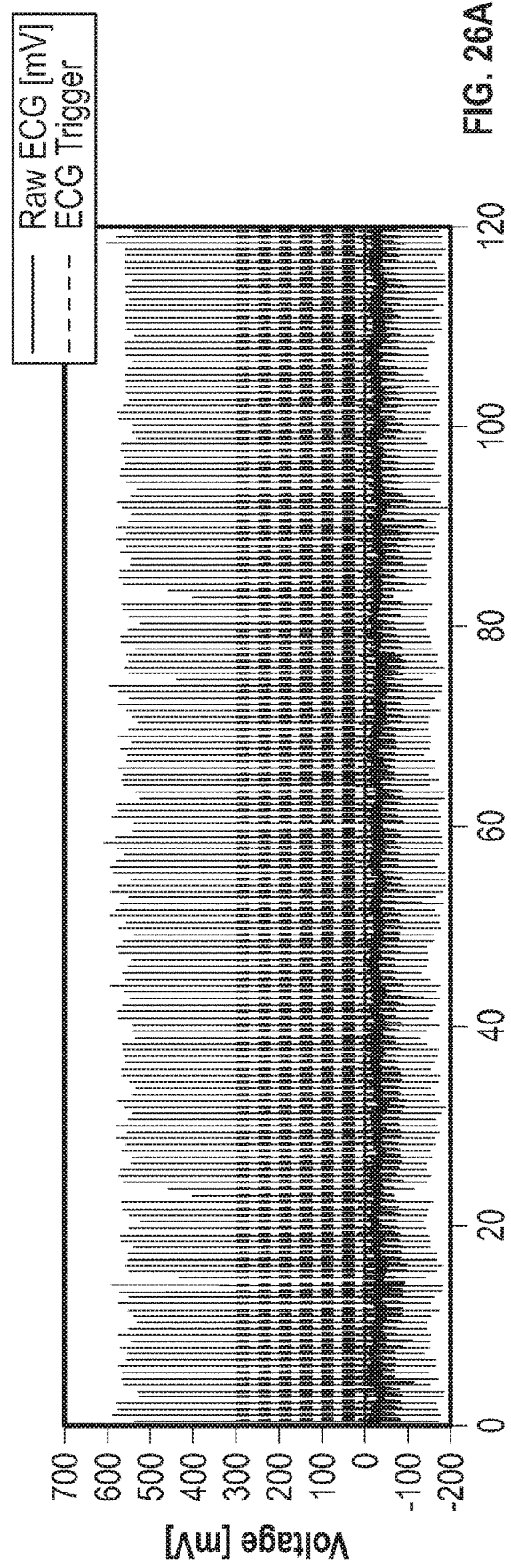
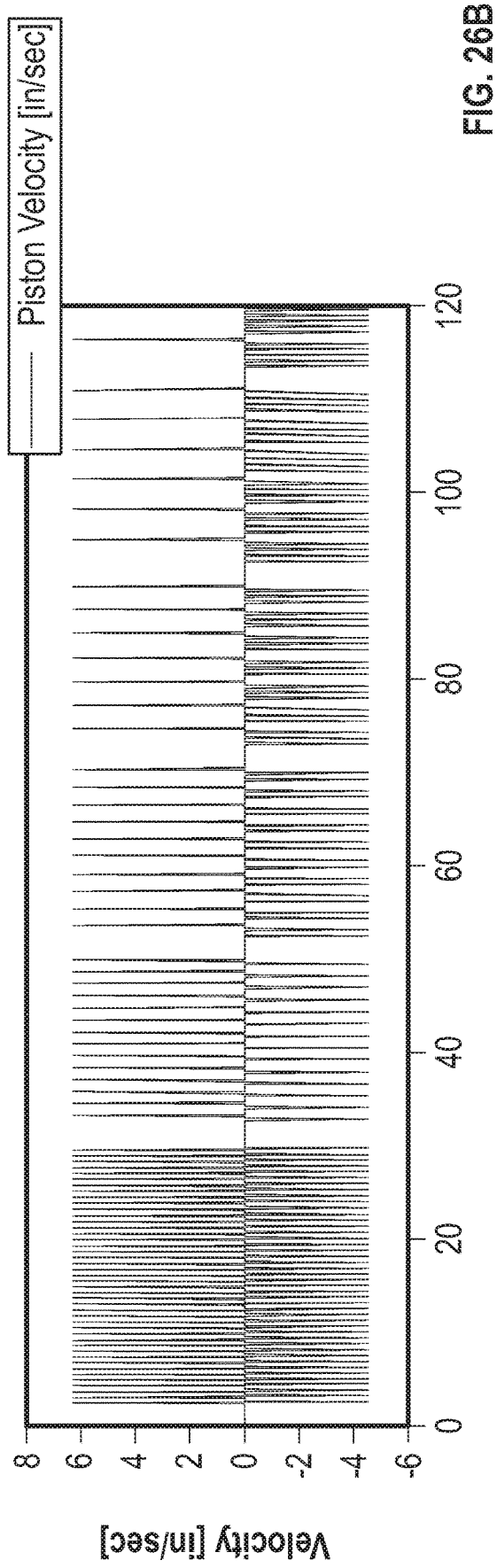

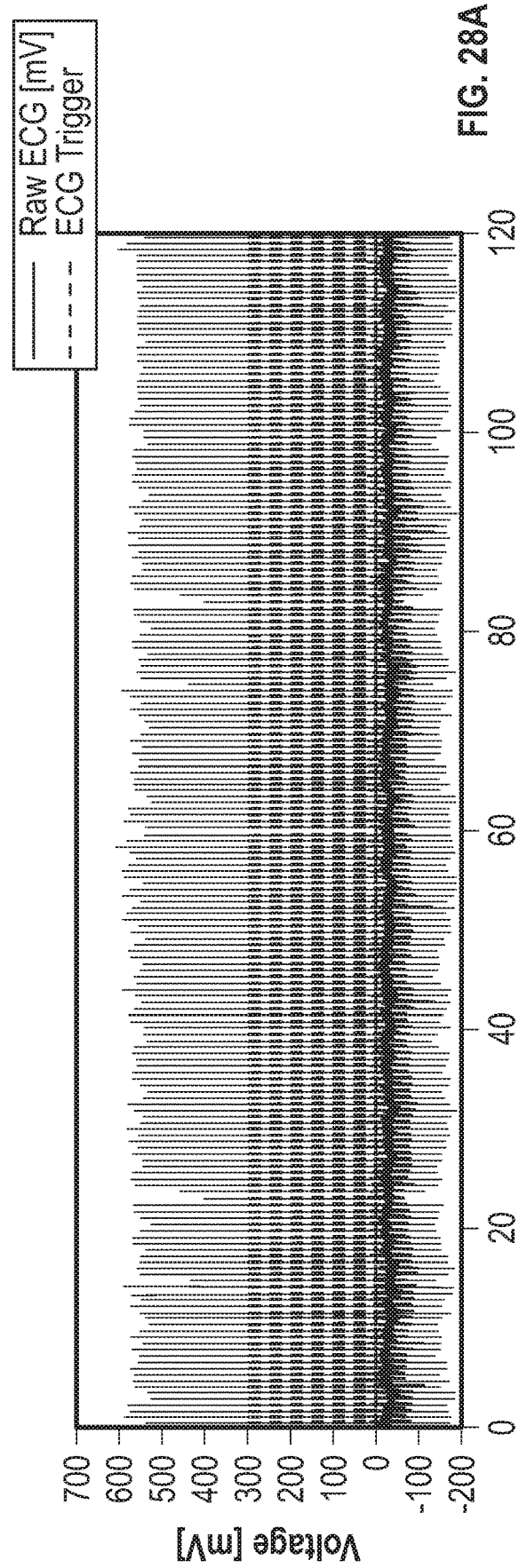
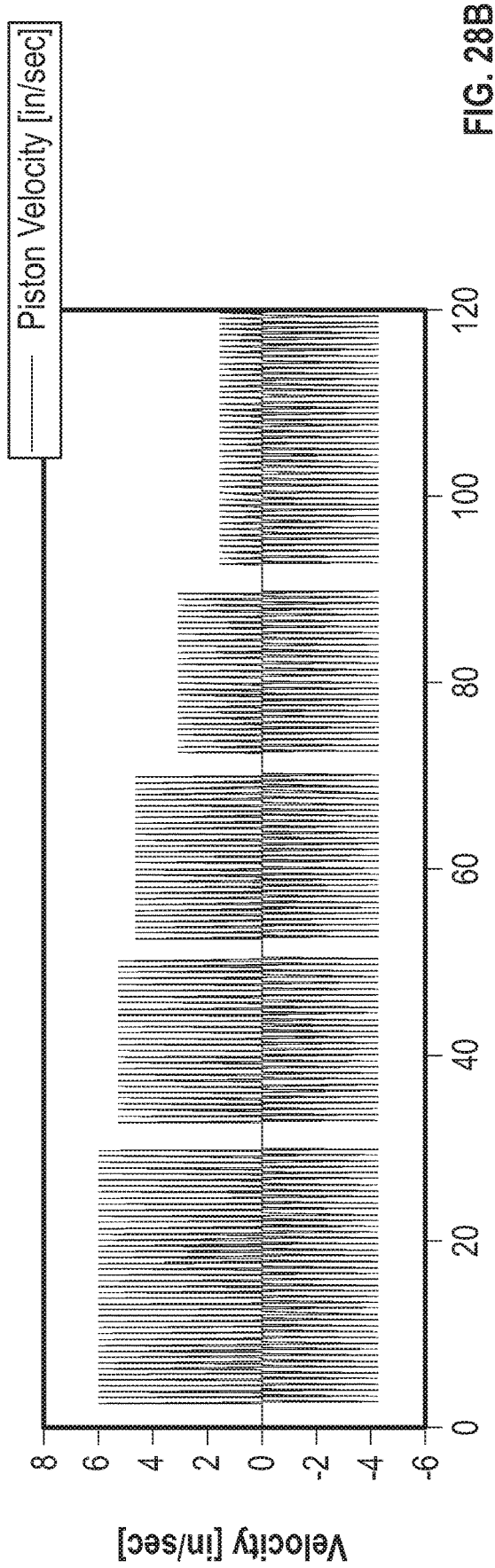
FIG. 28A
FIG. 28B

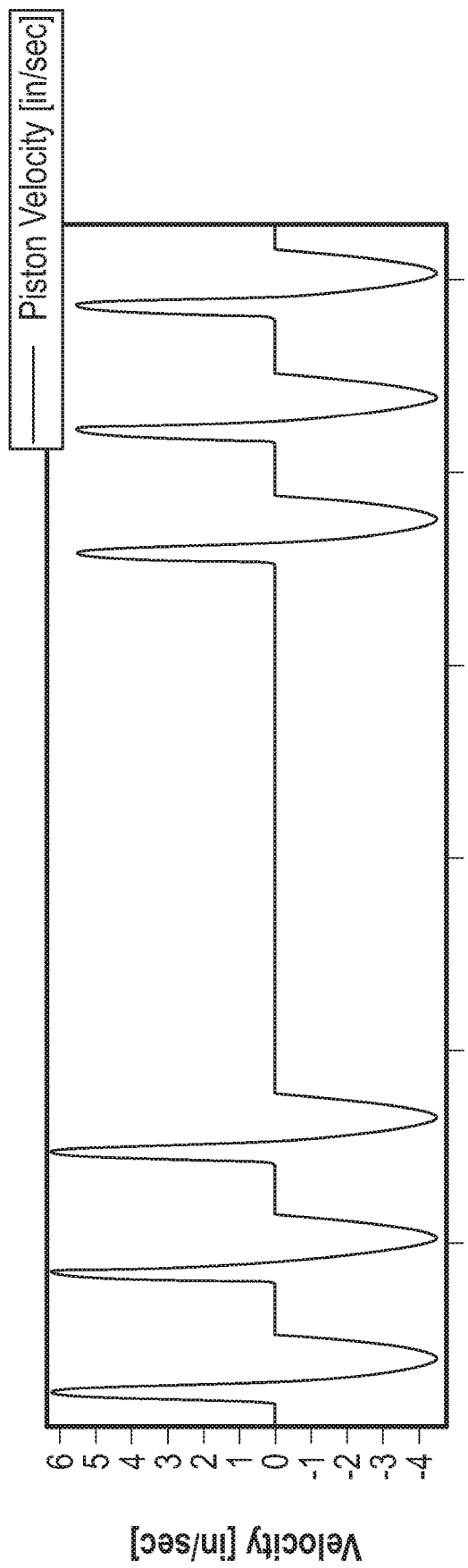
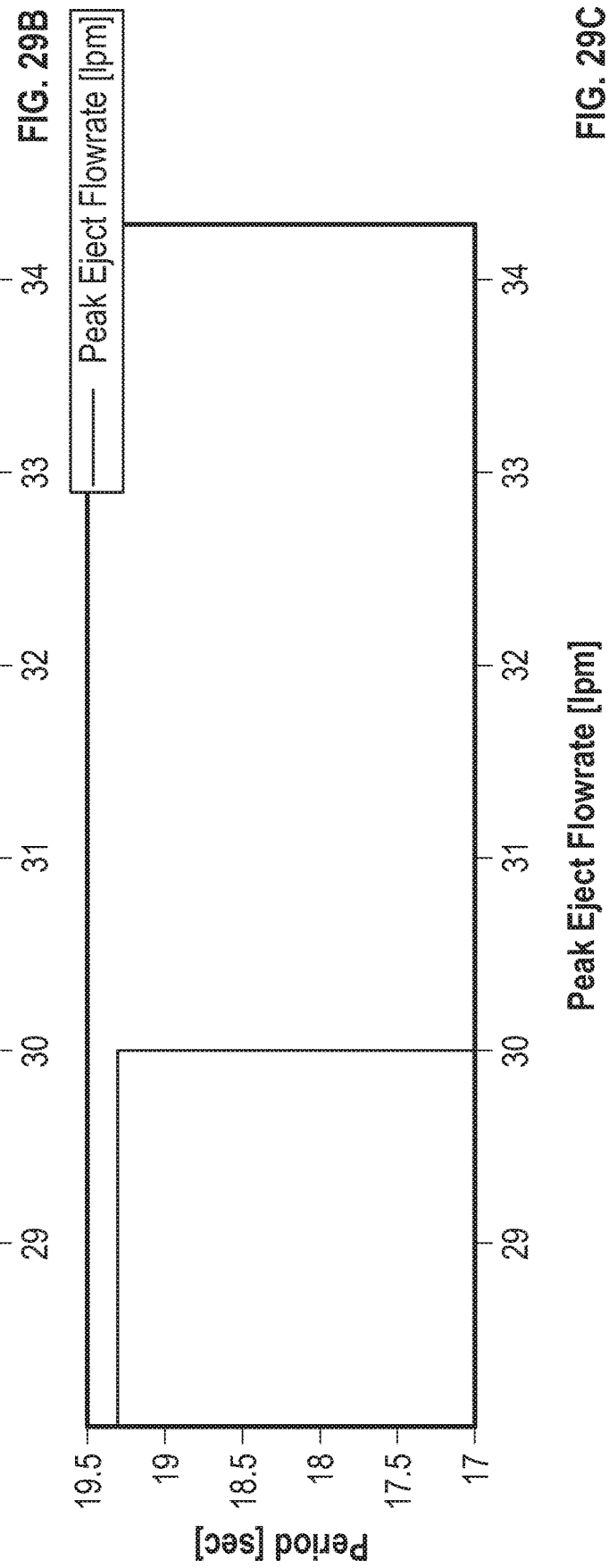
FIG. 29B
FIG. 29C

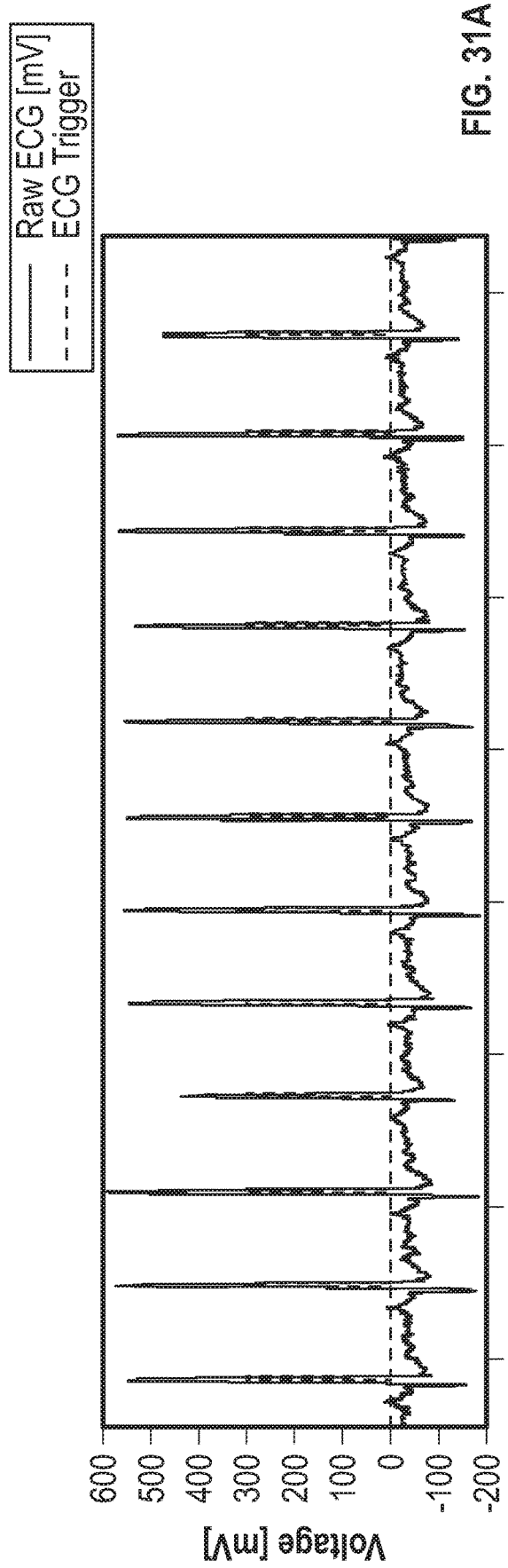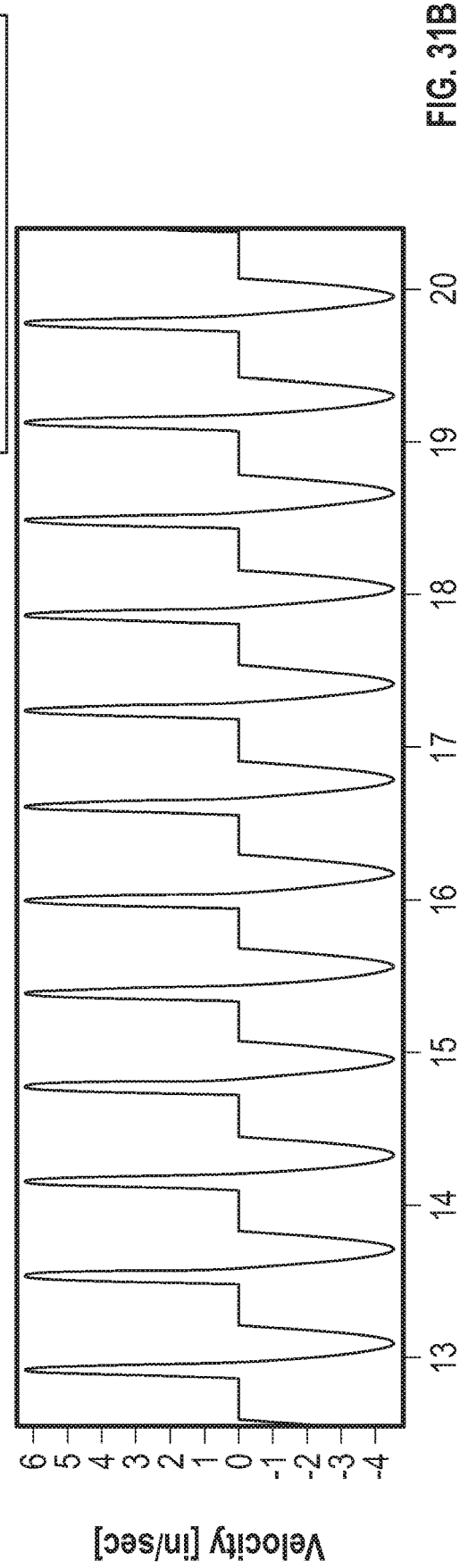

```
Discrete-Time FIR Filter (real)
-------------------------------
Filter Structure      : Direct-Form FIR
Filter Length         : 9
Stable                : Yes
Linear Phase          : Yes (Type 1)

Design Method Information
Design Algorithm      : equiripple

Design Options
Density Factor        : 16
Maximum Phase         : false
Minimum Phase         : false
SystemObject          : false Design Specifications
Sample Rate           : 128 Hz
Response              : Bandpass
Specification         : N,Fst1,Fp1,Fp2,Fst2,C
Filter Order          : 8
First Stopband Edge   : 1 Hz
First Passband Edge   : 5 Hz
Second Passband Edge  : 25 Hz
Second Stopband Edge  : 45 Hz
Stopband1Constrained  : true
PassbandConstrained   : false
Stopband2Constrained  : true
First Stopband Atten. : 40 dB
Second Stopband Atten.: 40 dB Measurements
Sample Rate           : 128 Hz
First Stopband Edge   : 1 Hz
First 6-dB Point      : 7.0416 Hz
First 3-dB Point      : 8.6102 Hz
First Passband Edge   : 5 Hz
Second Passband Edge  : 25 Hz
Second 3-dB Point     : 32.182 Hz
Second 6-dB Point     : 34.1831 Hz
Second Stopband Edge  : 45 Hz
First Stopband Atten. : 40.0873 dB
Passband Ripple       : 16.2835 dB
Second Sropband Atten.: 40.0646 dB
First Transition Width: 4 Hz
Second Transition Width: 20 Hz Implementation Cost
Number of Multipliers              : 9
Number of Adders                   : 8
Number of States                   : 8
Multiplications per Input Sample   : 9
Additions per Input sample         : 8
```

```
Numerator:
-0.10743380681617481
-0.28107652606745265
-0.18320067362901857
 0.28320274073468138
 0.57562139022484404
 0.28320274073468138
-0.18320067362901857
-0.28107652606745265
-0.10743380681617481
```

ELECTROCARDIOGRAPHY TRIGGERED PISTON PUMP

CROSS REFERENCE TO RELATED APPLICATION

This application claims priority to a U.S. Provisional Application No. 62/567,916 titled "ELECTROCARDIOGRAPHY TRIGGERED PISTON PUMP" filed on Oct. 4, 2017.

STATEMENT REGARDING FEDERALLY SPONSORED RESEARCH OR DEVELOPMENT

Not applicable.

REFERENCE TO A "SEQUENCE LISTING", A TABLE, OR COMPUTER PROGRAM

Not applicable.

DESCRIPTION OF THE DRAWINGS

The drawings constitute a part of this specification and include exemplary examples of the ELECTROCARDIOGRAPHY TRIGGERED PISTON PUMP, which may take the form of multiple embodiments. It is to be understood that in some instances, various aspects of the invention may be shown exaggerated or enlarged to facilitate an understanding of the invention. Therefore, drawings may not be to scale.

FIGS. 20A and 20B each comprise one half of the diagram of the operating code (which was divided due to the size), wherein the halves are joined at the dashed line for each drawing to create the full disclosed operating code. The inputs to the operating code are seen on the left side of the model. These can originate from simulated signals for a computational analysis or physical signals taken from hardware on an embedded target. The Encoder Processing and ECG Trigger ID process the signals that would originate from the quadrature encoder counter IC and the EKG shield, respectively. The Operating Controls subsystem integrates the sensor signals and the ECG trigger information into motion commands for the actuator. The Overwrite and Error Control subsystem monitors the actions of the system to prevent possible failure states. The Readback Processing subsystem calculates metrics on the system that are used to monitor system function for safety and documentation. Signals returned from this code are connected to numbered ports, signals ending in a termination block are not.

FIGS. 21A and 21B each comprise one half of the diagram of the operating controls subsystem code (which was divided due to the size), wherein the halves are joined at the dashed line for each drawing to create the full disclosed operating controls subsystem code. The Operating Controls subsystem code is grouped into three sections: Action to Motor, Operating States Table, and Subsystem Governs Actuation Motion. The Action to Motor determines the timing and magnitude characteristics of the motion profile, which are connected to the hardware configuration of the pump (e.g. piston size, actuator being used). The Operating States table integrates timing values with the trigger signal and intended operating mode of the pump. Governs Actuation Motion develops the velocity profile to be taken by the piston (e.g. sinusoidal, square) during a pumping cycle and produces the motion command in the form a Frequency Waveform value that is proportional to the intended velocity of the piston at a given time point. The main return information for this subsystem is: enable motion logical value, direction of piston motion, velocity of piston.

In FIGS. 24(a)-(c), two second gaps were programmed into the experimental control code to produce visible separation in the experimental data. The pump is capable of transitioning to different cycle periods throughout the course of testing.

FIG. 24(b) provides the recorded signals showing the pump action with variance in the cycle period that is shown in FIGS. 24(a) and 24(c), wherein the graph is providing a measure of the piston velocity over time.

FIG. 24(c) provides the recorded signals showing the pump action with variance in the cycle period that is shown in FIG. 24(a), wherein graph produced provides the cycle period over time.

FIG. 25(a) provides a focused plot of the signals for cycle period results for the 0.30 second cycle period segment at the end of the analysis, measuring the voltages of the Raw ECG and ECG Trigger over time.

FIG. 25(b) provides a focused plot of the signals for cycle period results for the 0.30 second cycle period segment at the end of the analysis, measuring the piston velocity over time.

FIG. 26(a) provides the recorded signals of the pump performance with varying fills per eject over the course of an ECG triggering signal, herein measuring the voltages of the Raw ECG and ECG Trigger over time.

FIG. 26(b) provides the recorded signals of the pump performance with varying fills per eject over the course of an ECG triggering signal, herein measuring the piston velocity over time.

FIG. 26(c) provides the recorded signals of the pump performance with varying fills per eject over the course of an ECG triggering signal, herein measuring the fills per eject.

FIG. 28(a) provides the recorded signals showing the change in peak ejection flowrate, which is the calculated runtime variable based on the stroke volume knob selection, wherein the signals measured are the voltages over time for the Raw ECG and ECG Trigger.

FIG. 28(b) provides the recorded signals showing the change in peak ejection flowrate, which is the calculated runtime variable based on the stroke volume knob selection, wherein the signal measures the piston velocity over time.

FIG. 29(b) provides the recorded signals that highlight the change in peak ejection flowrate between a settings change, with the programmed pause of two seconds, wherein the signal measured is the piston velocity over time.

FIG. 29(c) provides the recorded signals that highlight the change in peak ejection flowrate between a settings change, with the programmed pause of two seconds, wherein the signal measured is the peak eject flow rate for the cycle period.

FIG. 31(a) provides the recorded signals of the highlight of the 0 ms delay region illustrating syncopation with the QRS complex, wherein the recorded signals are the voltages of the Raw ECG and ECG Trigger over time.

FIG. 31(b) provides the recorded signals of the highlight of the 0 ms delay region illustrating syncopation with the QRS complex, wherein the recorded signal is the piston velocity over time.

FIG. 33(c) provides the filter design characteristics in a design topology.

FIG. 33(d) provides the numerator values of the filter design characteristics.

FIELD OF THE INVENTION

Figure 1:
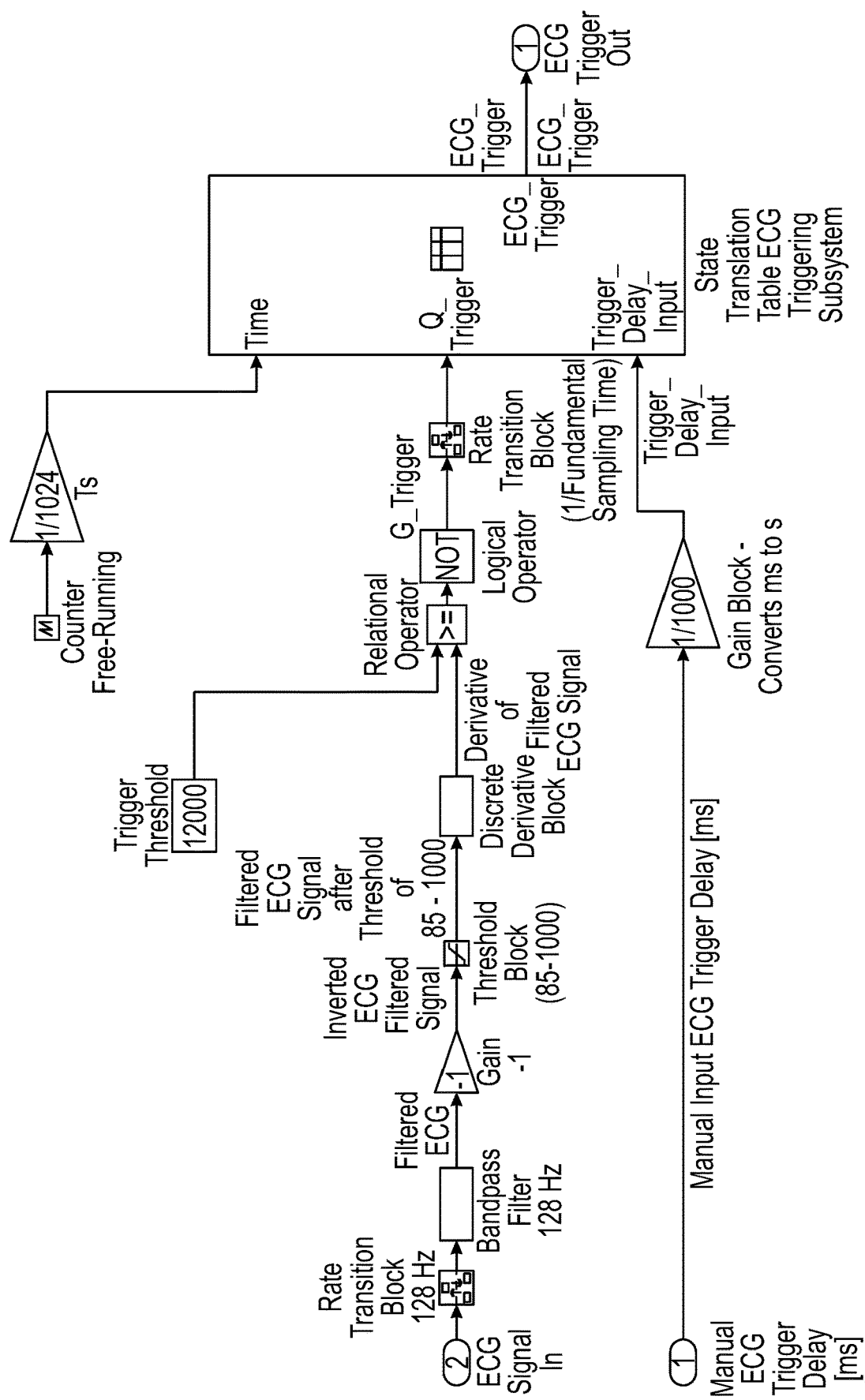
FIG. 1 depicts the logic diagram for the preferred embodiment of the Electrocardiography (ECG) Trigger subsystem. The inputs for this system are the ECG signal and the trigger delay. The output is the trigger pulse waveform.
Figure 2:
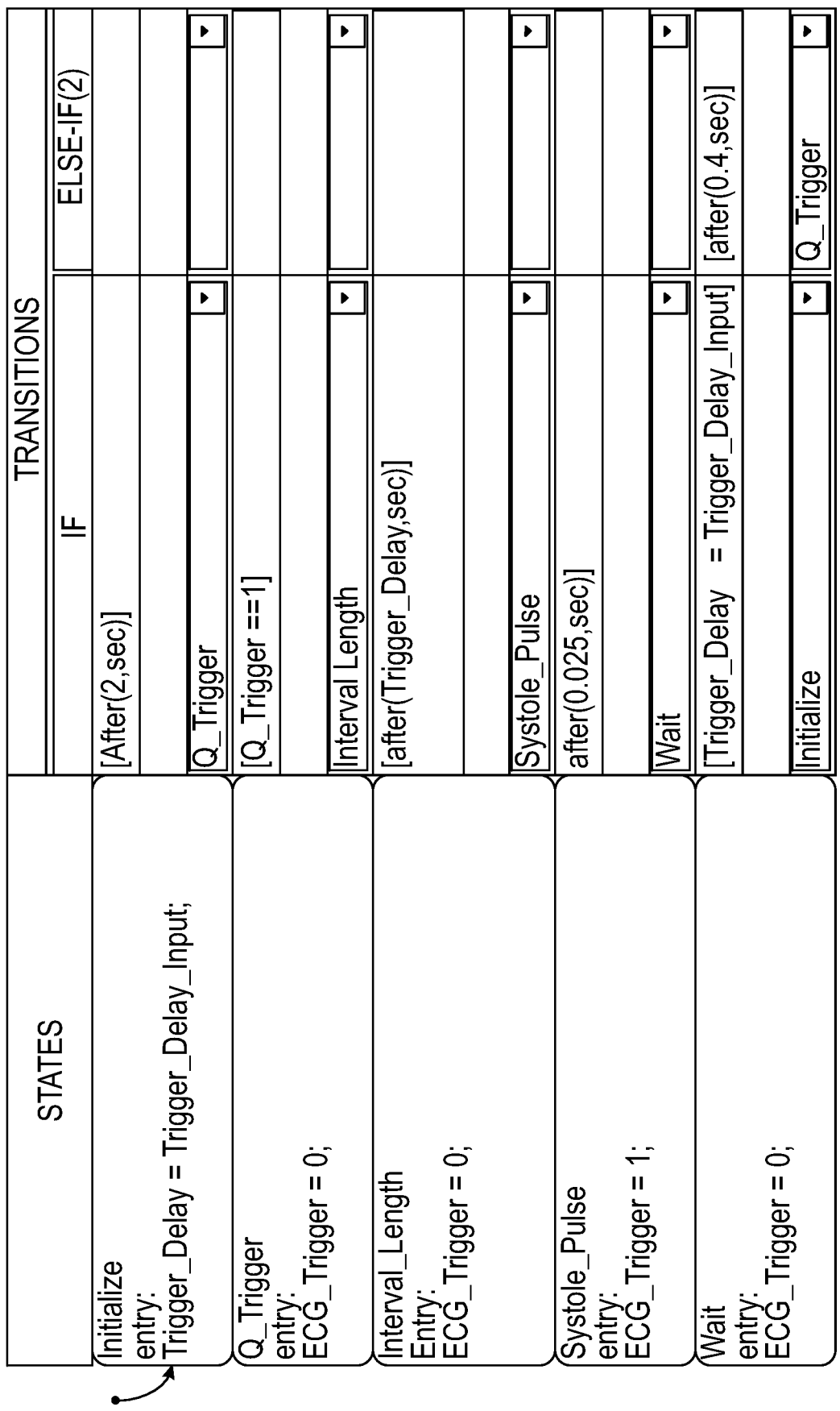
FIG. 2 provides an example logic table governing the creation of the trigger pulse. The Initialize state has a 2 second delay for startup stability. The Systole_Pulse state controls the pulse width and is coded as 25 milliseconds. The Wait state controls the reset of the trigger pulse and return to the Q_Trigger state once the threshold of the Q-wave slope is detected.
Figure 3:
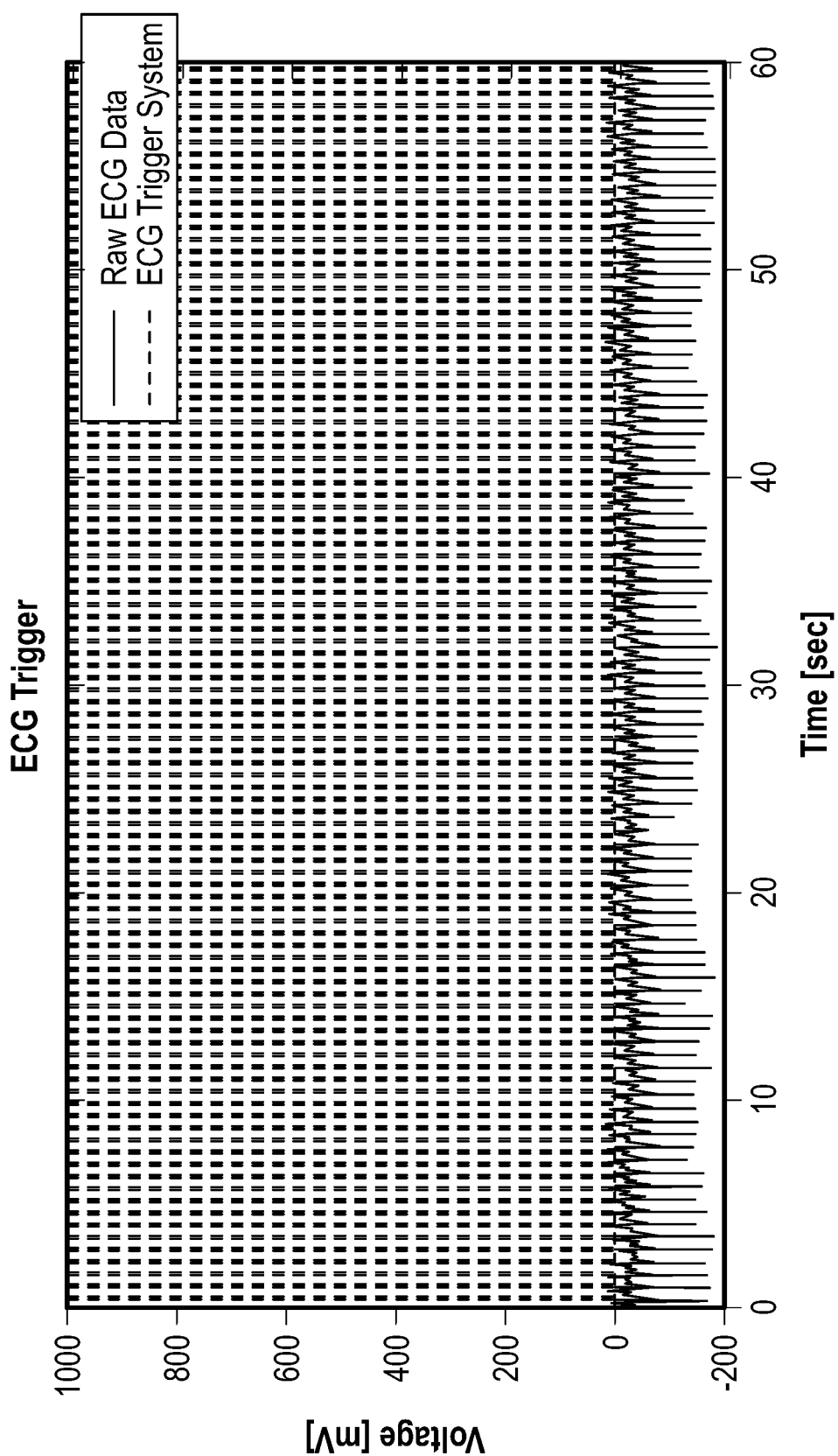
FIG. 3 shows ECG 16265 provided by the PhysioNET MIT-BIH Normal Sinus Rhythm Database. Raw Data is shown using an unbroken line, and the ECG trigger is shown using a dotted line. The trigger has been amplified by 1000 for visual clarity. A mean error of −0.0018 was calculated between the time of the R-wave peaks and systolic triggers.
Figure 4:
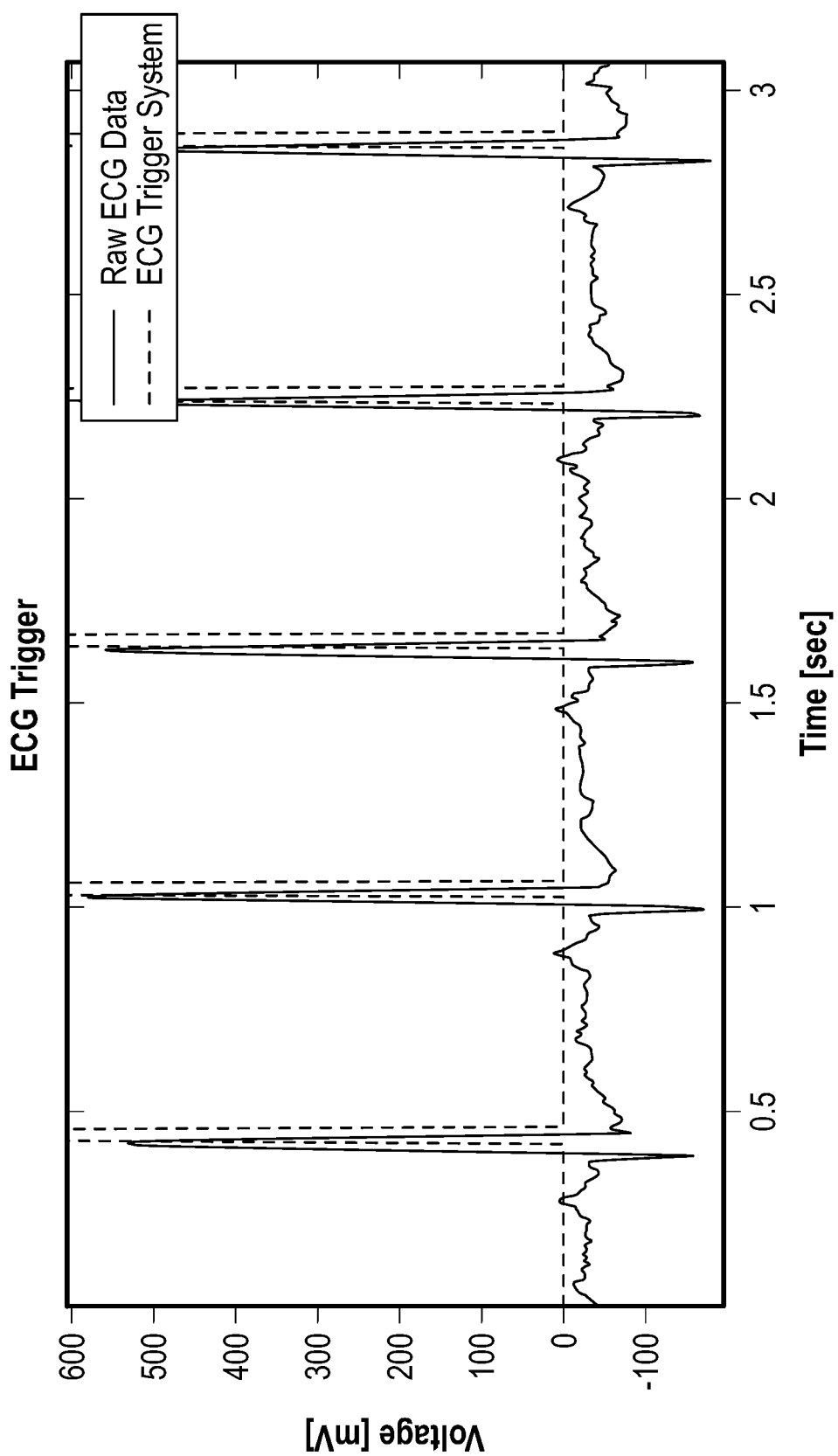
FIG. 4 shows the ECF 16265 from FIG. 3, zoomed in to 3 seconds. The delay from the Q-wave onset produces a trigger that coincides with the R-wave.
Figure 5:
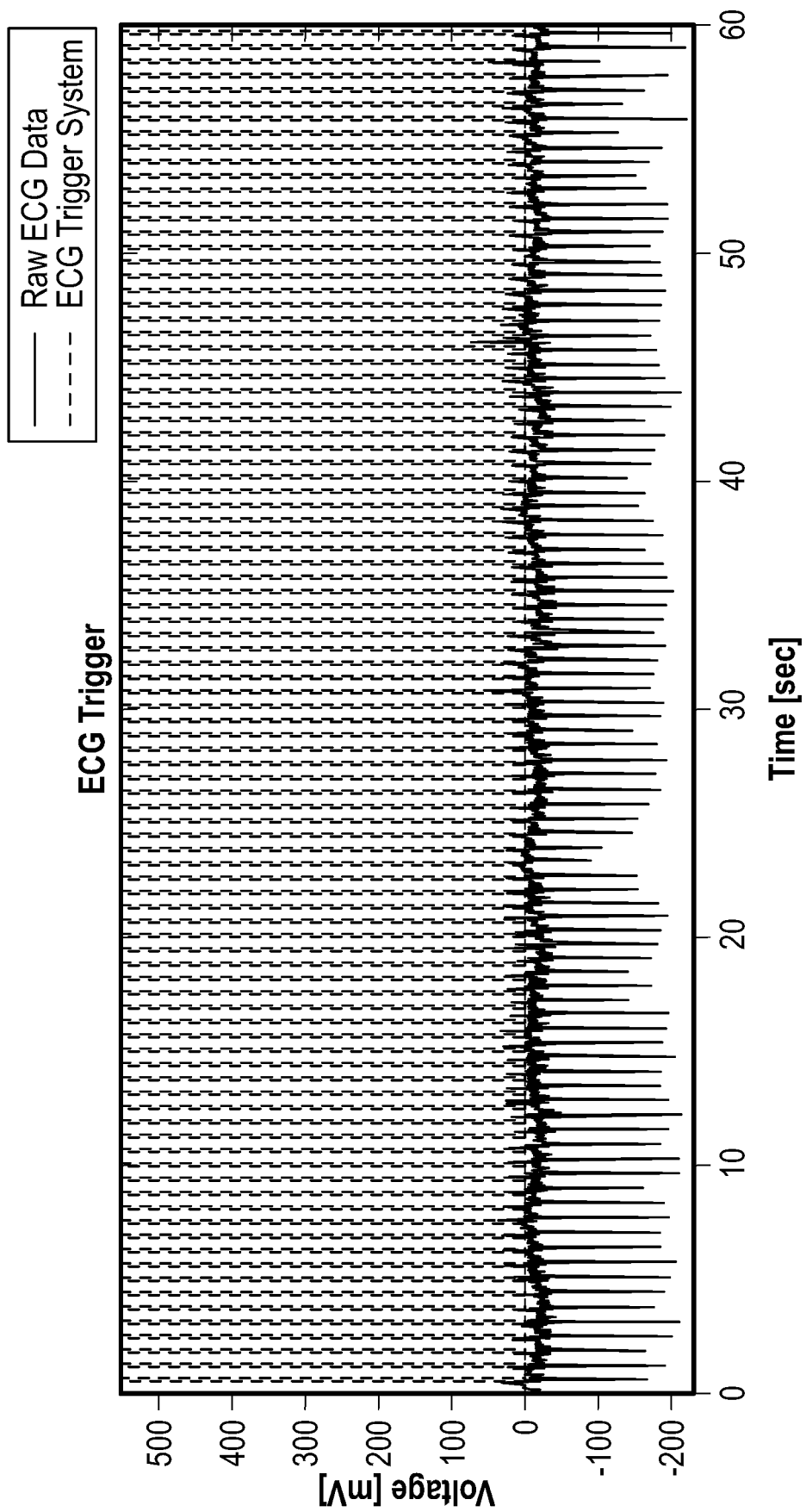
FIG. 5 shows the performance against 60 seconds of ECG 16420. A mean error of −0.0097 was calculated between the time of the R-wave peaks and the systolic triggers. This analysis illustrates the trigger working against a wandering baseline.
Figure 6:
FIG. 6 shows the performance against 60 seconds of ECG 16483. A mean error of −0.0095 was calculated between the time of the R-wave peaks and systolic triggers. The analysis shows the performance of the trigger against high noise in the ECG signal.
Figure 7:
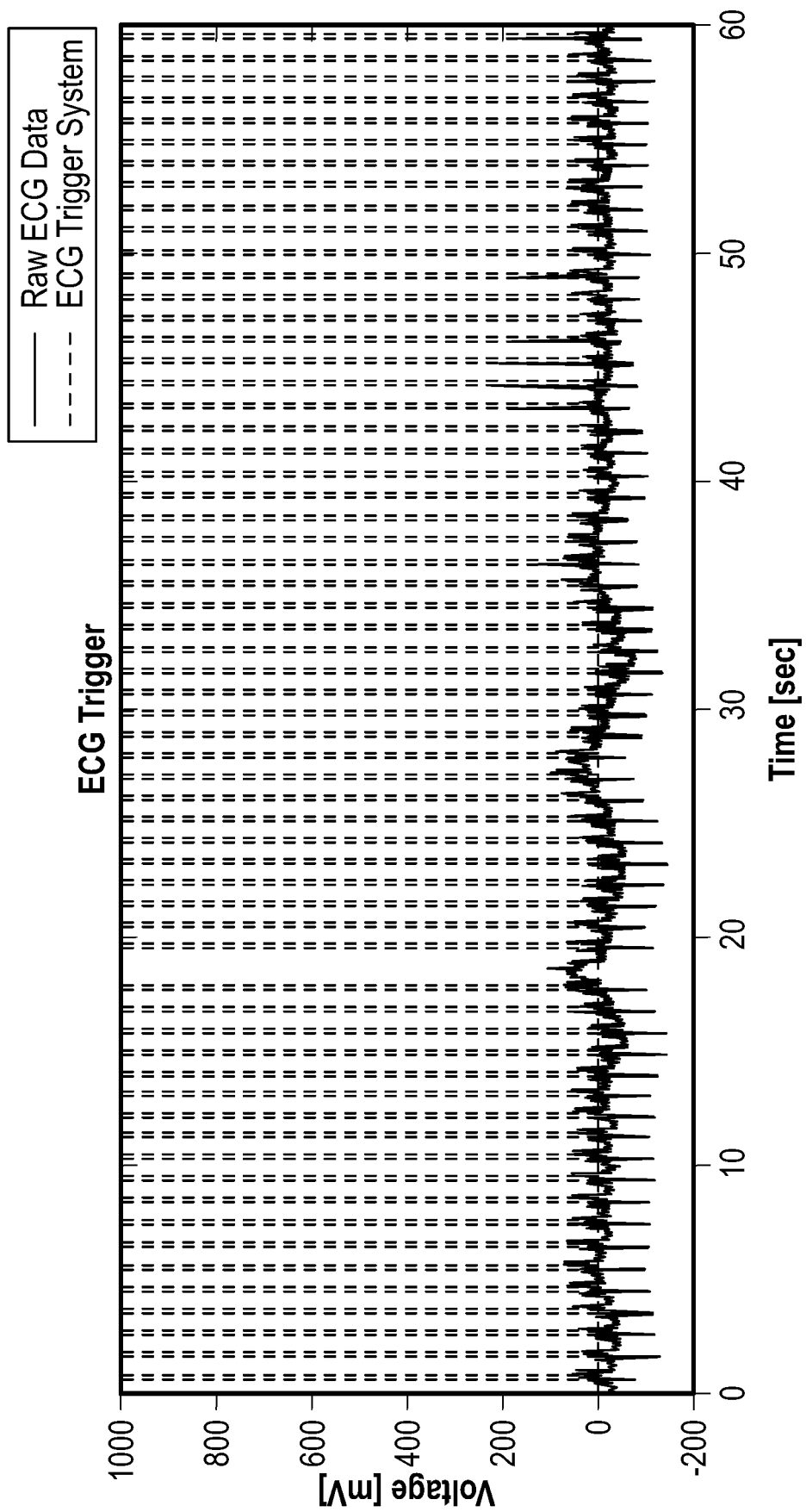
FIG. 7 shows the performance against 60 seconds of ECG 16272. Note that every trigger was accurate except for the one missed trigger at approximately 18 seconds. This is an example of a portion of an ECG that will not trigger a systolic moment; the QRS complex is not completely formed in this segment of the signal.

The disclosed device is generally related to the field of pulsating, positive displacement pumps. More specifically, the disclosed pump is related to the field of pumps used in cardiovascular operations, which can simulate the pumping action of a heart.

BACKGROUND OF THE INVENTION

The disclosed device seeks to augment pressure wave forms through syncopation of the hardware with a physiological signal; in this case, the electrocardiogram. Pulsatile pump integration with a physiological system exists, but has traditionally been used to supplement flow. Timing action of a flow system with the cardiovascular system has also been shown, but has been embodied through regulation of the cardiac rhythm using a pacemaker. The disclosed device allows for filling to be achieved over multiple cardiac cycles, which has not been shown in the field of invention.

SUMMARY OF THE INVENTION

The invention disclosed is a positive displacement pump that triggers with the beating of a mammalian heart, through the monitoring of an ECG signal is disclosed. The pump is capable of syncopating the ejection of the fluid with the events occurring in the cardiovascular system based upon a programmed delay. The novelty of this system stems from the adaptable control architecture designed to augment the pulsatile characteristics of the cardiovascular system. This inventive concept could be expanded to encompass the augmentation (dampen or enhance) of pulsatile characteristics in any oscillating flow system. The disclosed design has the ability to minimize the impact of its filling action on the draw source by breaking up the filling over multiple heartbeats. It is also configurable to different pumping capacities through an interchangeable pump head, which could allow it to serve a variety of physiological models.

DETAILED DESCRIPTION OF THE INVENTION

The Electrocardiograph ("ECG") Triggered Piston pump is a biocompatible positive displacement pump that triggers with the beating of a mammalian heart. The pump is capable of being filled from a distal systemic artery and returning the drawn volume to a proximal systemic artery. The pump is control system implements a code section that accepts ECG data and indicates the onset of the ventricular systole in runtime. The triggering of the pump is based upon ECG events.

A digital filter in conjunction with threshold detection is designed to robustly identify the Q-wave of the peak in an ECG trace in runtime. By amplifying the high frequency content of the QRS complex, the user can detect when the Q wave onset crosses a threshold that exists above the background noise.

The disclosed design has the ability to minimize the impact of its filling action on the draw source by breaking up the filling over multiple heartbeats. It is also configurable to different pumping capacities through an interchangeable pump head, which could allow it to serve a variety of physiological models.

The positive displacement pump has controllable eject and fill sequences capable of being timed with the ECG trigger. The assembly comprises the following subsystems: frame, drivetrain, cooling, pump head, and electronics. The core functionality of the unit resides in the pump head and drive train, defined as the "pump unit." The electronics architectures provide the interface capability and the execution of functionality needed for the design.

Figure 8:
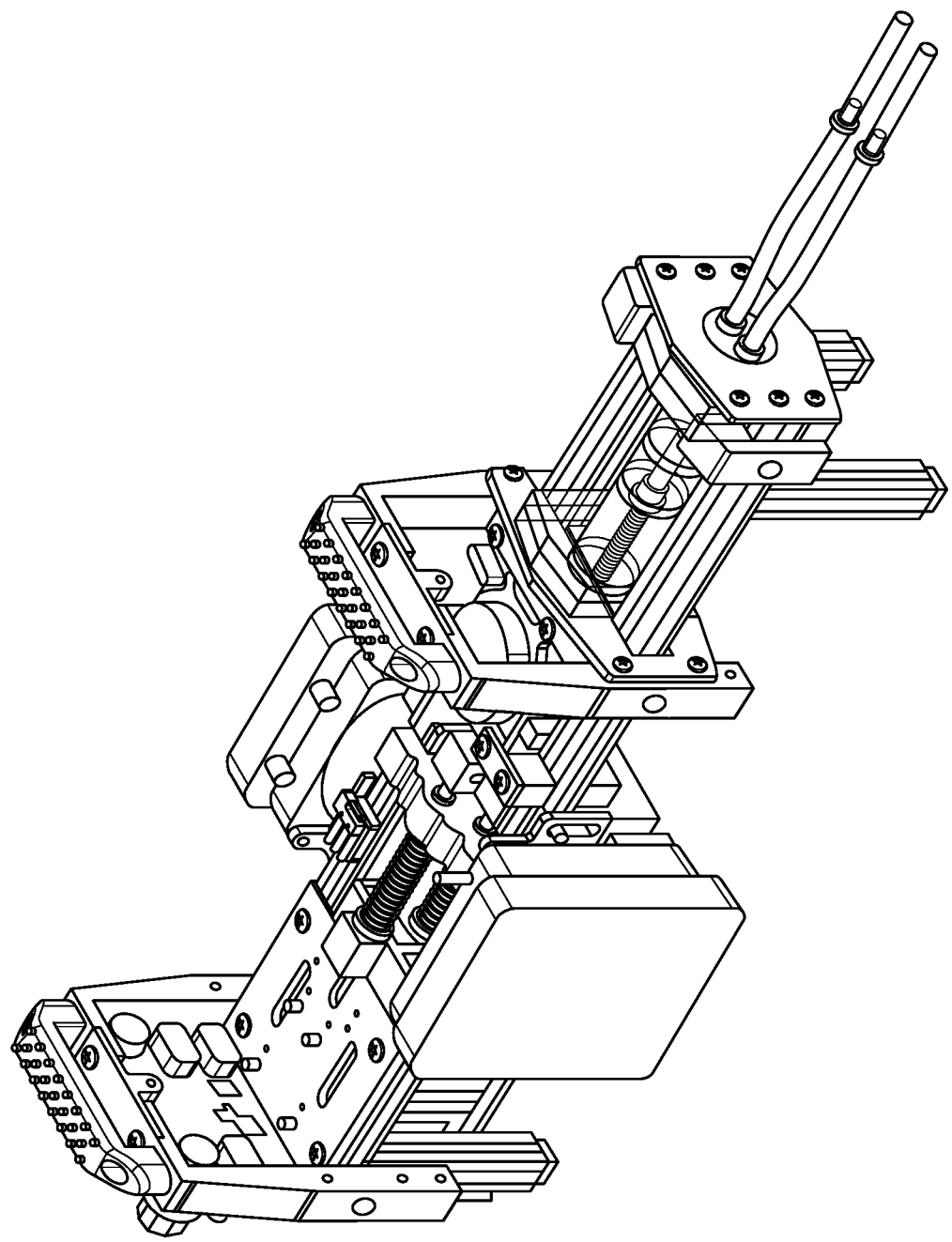
FIG. 8 provides an isometric view of the design with the electronics and case absent from the rendering.
Figure 9:
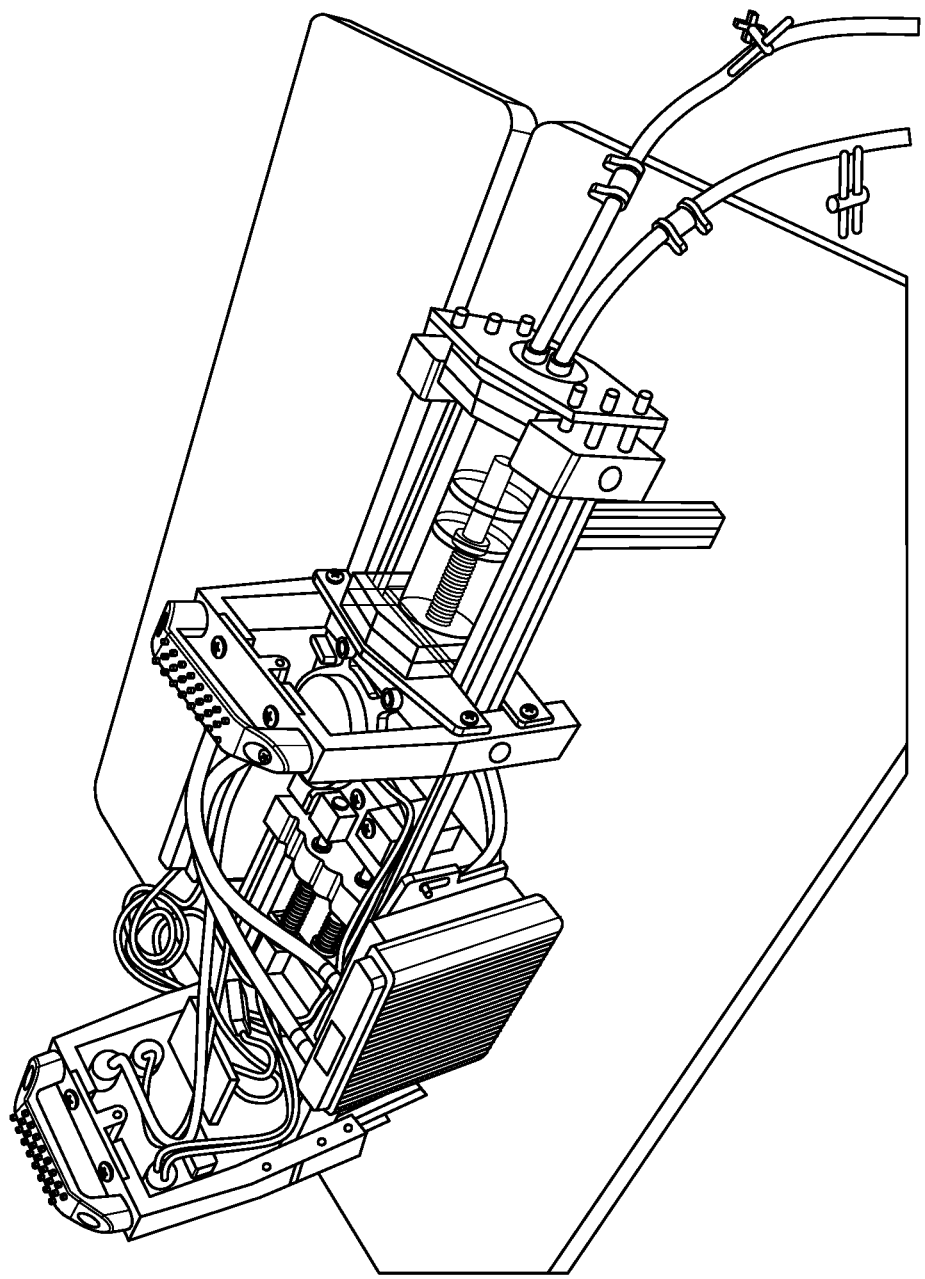
FIG. 9 provides an image of prototype system with the case removed to show the interior of the unit.
Figure 10:
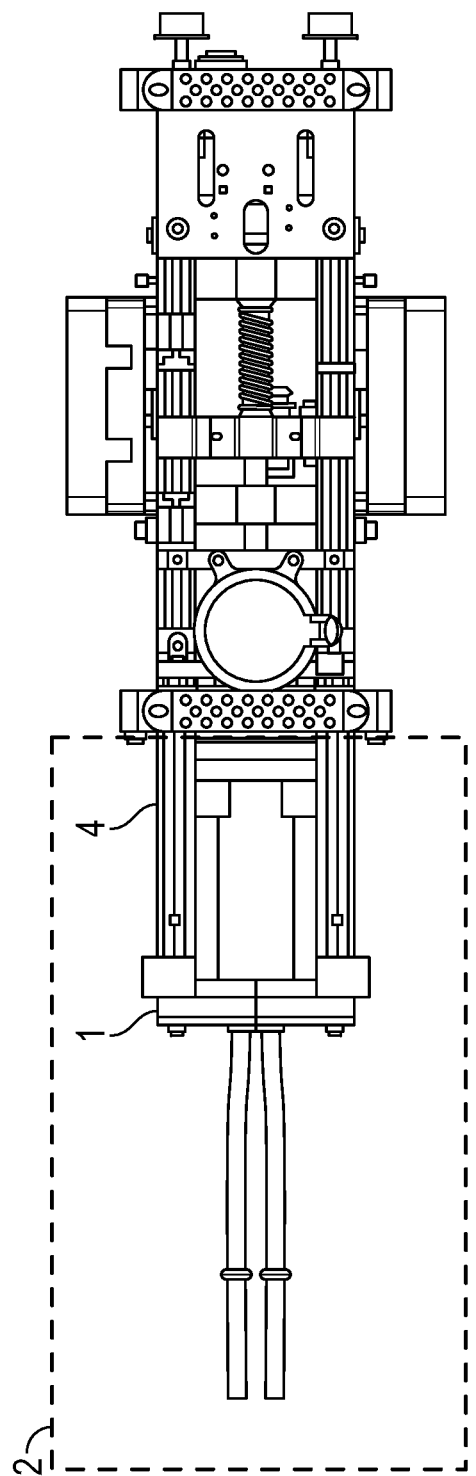
FIG. 10 provides a top view of the design with the pump head viewable. The mounting plate on the front is considered part of the frame and constraint assembly. The piston is not visible in this rendering, but is considered part of the drivetrain.
Figure 11:
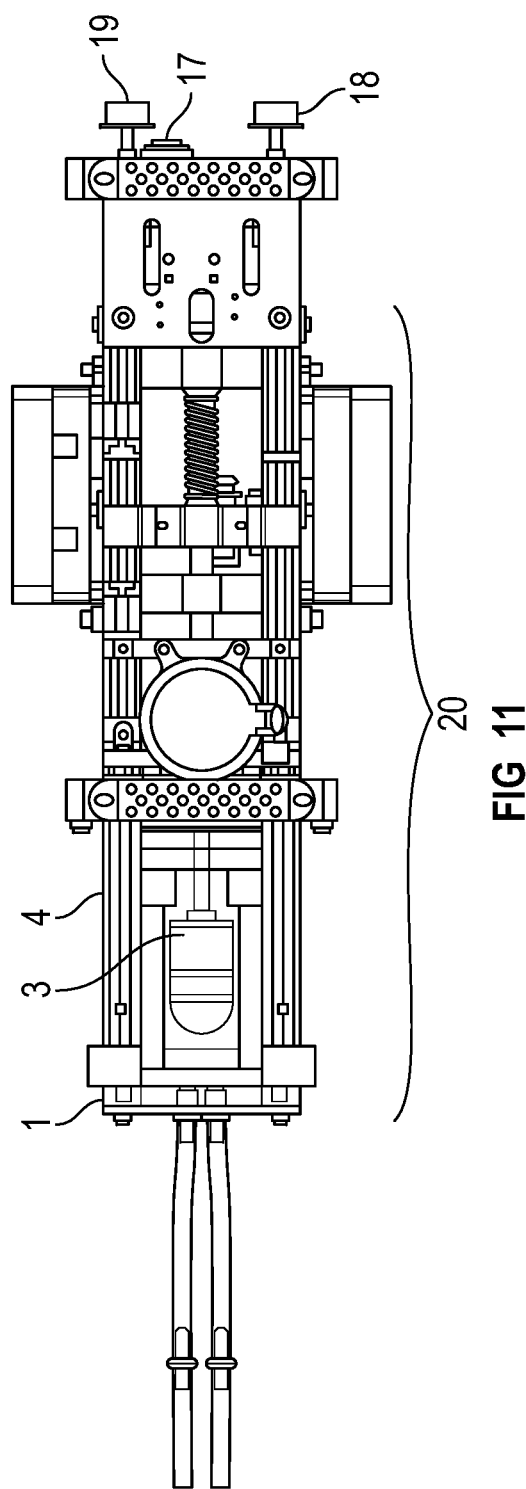
FIG. 11 provides an additional view of the top of the design with the pump head viewable. The stepper motor is obscured by the cooling head, while the limit hardware and spring assembly are visible. The piston is included in this subassembly to denote the hydro-mechanical interface in the design.

The device comprises a piston pump powered by a linear motion stepper motor drive unit is controlled by an embedded microcontroller. A CAD model of the unit is shown in FIG. 8. The embedded electronics are seen at the back of the embodiment depicted in FIG. 9. The design utilizes an extruded aluminum frame to provide the mounting point for the pump head, drivetrain, and electronics subsystems. Each of these subsystems can be disconnected from the interfacing units and removed individually from the frame.

Pump Head:

The pump head is stationed at the end of the unit for ease of access to the investigation space for the evaluation trials. In the prototype embodiment shown in FIG. 9, the prototype's piston design has a 1.5" diameter bore (~1.76 in$^2$ piston face) with a 2.75" travel (4.84 in$^3$ max stroke volume), though one skilled in the art will recognize that alternative dimensions may also be successfully employed. The dimensions here equate to a 3.81 cm diameter bore (~11.40 cm$^2$ piston face) with a 6.99 cm travel (~80 mL max stroke volume). In the preferred embodiment, Poly(methyl methacrylate), also known as PMMA or acrylic, is used as the material for short-term biofluid compatibility, though other materials may be used. To allow for fluid operation, a lubricant (such as Perfluoropolyether (PFPE) based lubricant) is used to grease the piston and prevent protein binding on the fluid contact surfaces. In the preferred embodiment, the prototype piston is also constructed of PMMA and uses nitrile rubber seals (e.g., Buna-N seals).

The pump casing comprises a feed line and a return line. These connections are comprised of a barb adapter connecting tubing to acrylic pump casing, flexible polymer tubing, high flow check valve, and a three-way barb or luer lock valve (such as those produced by Qosina™). The barbed connections on the check valves can be reinforced with tubing clamps to prevent failure during operation. The feed line has the check valve enabling flow towards the unit, and preventing back flow. The return line enables flow away from the unit. The two lines are identical, save for the orientation of the check valve.

In the preferred embodiment, the pump casing is secured using rear guides that follow the channel of the frame and a front mounting plate. The mounting plate secures the aluminum front plate directly to the frame and clamps the front pump casing plate to support mounts extending from the frame, both using known fastening methods such as bolts. The piston is attached to the drivetrain in a manner that constrains translation (e.g., a leadscrew nut) and prevents rotation (e.g., set screws).

Drivetrain:

In the preferred embodiment, the actuator is a linear stepper motor connected to a spring system providing translating motion of the piston. The prototype embodiment's linear stepper motor is an Anaheim Automation 23AV106DX12-AE drive: 3.0 A/phase, 0.250" pitch, anti-backlash nut, and encoder. Springs reduce the force required of the stepper motor during ejection, enabling higher speeds. Force and velocity are inversely related in a linear motion actuator, while piston area and velocity are also inversely related when considering the geometry needed to produce a pulse wave. This presents force and piston area as positively related, with the later compounding the effects of friction and further increasing the amount of force needed for motion. The application requirements placed the emphasis on the pulse wave generated by the ejection of the system. This enabled the design to incorporate a low speed high force fill sequence to load the spring system and a fast ejection speed supported with a high force sourced from the springs.

The actuator comprises a spring system, motion guides, and limit switches. In the preferred embodiment, the spring system uses two springs to balance the force about the central axis of the driveshaft. These springs may be optionally exchanged to match the performance required by the geometry of the pump head size in use; for instance, larger pump head requires stiffer springs. Motion guides prevent rotation of the driveshaft and keep the shaft aligned with the pump head assembly. Hard stops mounted to the frame prevent over travel of the motion system that could lead to damage of the pump head. Limit switches enable calibration routines to be executed and safe stop functionality that protects the actuator from collisions with the hard stops.

Cooling System:

To achieve the specified speeds from the linear actuator in the preferred embodiment, the maximum driving voltage rated for the stepper motor was used (for the prototype embodiment, 48 VDC). The operating period of the pump and the final closed case design demanded that an active cooling solution was employed; however, additional embodiments, such as those without a closed-case design may not require a cooling system. Two closed circuit liquid cooling units were installed to opposing sides of the stepper motor drive housing. The radiator units are placed on opposing sides of the pump to dissipate heat away from the pump and the experimental region at the front of the design. Previous attempts with heatsinks and case fans were unsuccessful. This final design mitigates the heat generation of the drives and prevents other components from heat damage.

Figure 18:
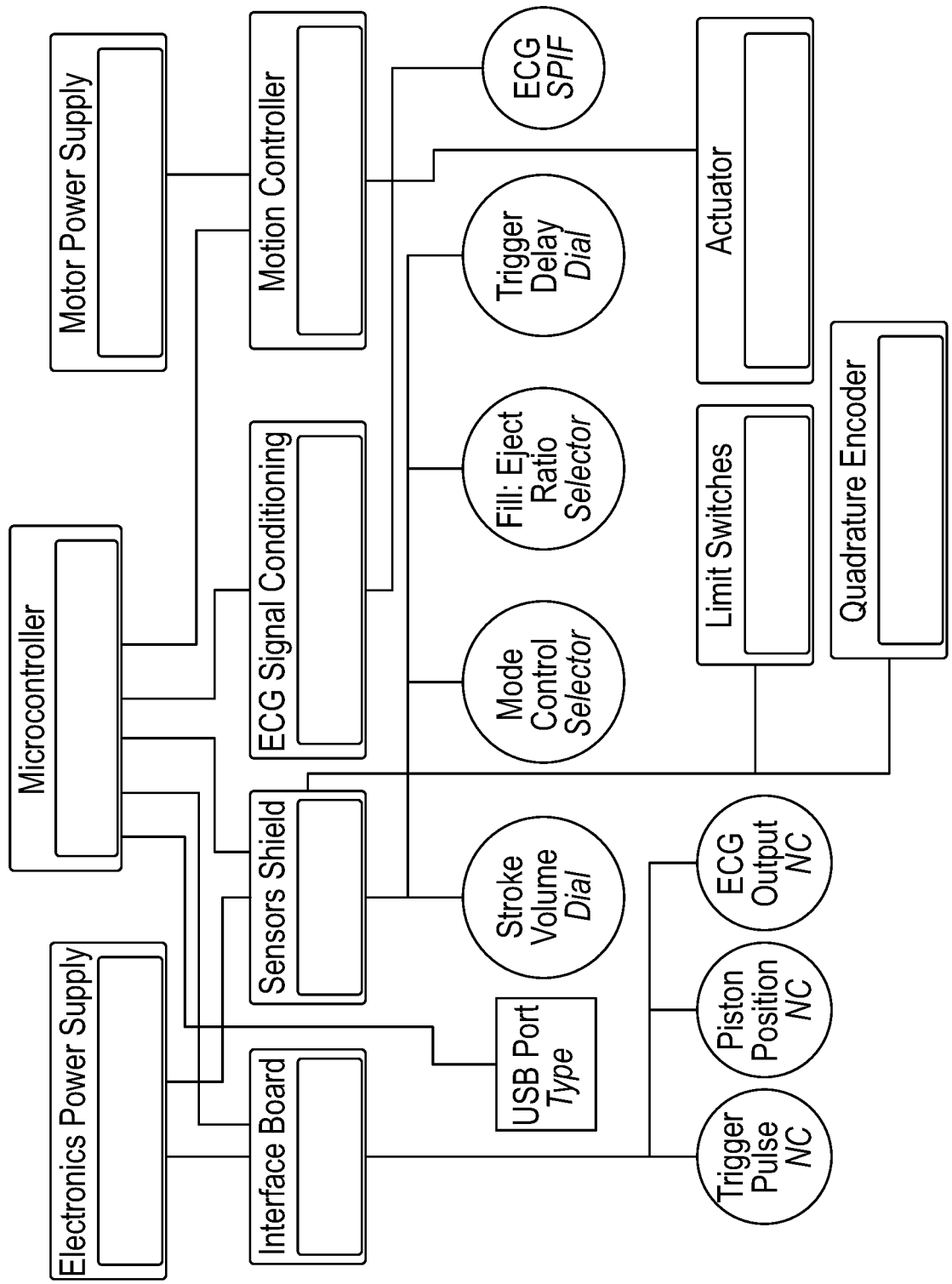
FIG. 18 provides a diagram of the electrical components and their connections in the preferred system.

Electronics:

The embedded processor executing the control code for the triggered pump is a microcontroller, which is the central unit in the electronics subsystem (FIG. 18). The processor is preferably mounted in an Arduino Mega 2560 R3 package to assist development, integration, and replaceability of the part in the event of damage. This processor and package variant is widely available and heavily documented with an array of products (e.g. shields) that can be used to expand the functionality of the design. The processor is accessible through a USB Type-B connection on the back panel of the pump.

Initial prototyping work was executed with a stepper driver (MCB05641, Anaheim Automation, USA) that was controlled with a step clock source. The overhead motion control processing and frequency generation capability of the microcontroller necessitated a design change to an embedded motion control chip (powerSTEP01, ST Micro, Switzerland). This motion control chip offloads a large amount of the processing needed to execute motion commands, is capable of smoother motion profiles, and eased the integration with the microcontroller through the shield-oriented nature of the X_NUCLEO_IHM03A1 package.

FIG. 18 provides a diagram of the electrical components and their connections in the system. The microcontroller is the central processor for the system and is the unit executing the control code. The microcontroller is connected to four separate circuit boards: (1) Interface Board, (2) Sensors Shield, (3) ECG Signal Conditioning Board, and the Motion Controller. The Interface Board and Sensors Shield are custom electronics designed and fabricated for this system. The ECG Signal Conditioning Board and the Motion Controller are generated using known technology—either through a purchased solution or construction using methods and devices known in the art. The Interface Board provides the output signals from the system to a series of BNC connectors—the ECG Trigger Pulse, Piston Position Voltage Signal, and ECG Voltage Signal. The Sensor Shield connects to the dials controlling the operation of the unit, as well as internal connections to the limit switches and motor position encoder. The ECG Signal Conditioning shield connects via headphone jack to the 3-lead ECG wiring harness. The motion controller drives the actuator through a high-power connection. There are two power supplies that power the electronics and the motor, respectively. A communications port in the form of a USB connection can be made directly to the Microcontroller for serial communication and installing software on the unit.

Peripheral sensor signals are aggregated through the Sensor Shield to provide a centralized interface to the microcontroller. This shield has connections to the user control elements on the rear of the pump, as well as the motion control limit switches and quadrature encoder.

The user enacts control of the pump actions using dials and selectors. A touchscreen interface can also be utilized; however, dials and selectors are preferred as more conducive for gloved operation. The dials are continuously variable potentiometers that allow for fine-tuning of stroke volume and trigger delay. In one embodiment, the stroke volume is rounded to the nearest 0.1 mL (0-30 mL) and the trigger delay is rounded to the nearest millisecond (1-100 ms) when used in the control code.

The selector switch allows for pump mode selection and selection of the ratio of fills to eject (1:1 to 6:1). The limit switches are binary normally open (NO) with local low (GND) read by the microcontroller and closed upon contact with logical high 5V read by the microcontroller. The quadrature encoder is a 2500 counts per revolution three channel output model operating at TTL levels: A, B and Index. This enables a theoretical positioning measurement of the piston to the nearest 0.0001 in (0.00025 cm). In one embodiment, a 11.4 cm2 pump face and an ideal actuator is provided, equating to a 3-microliter accuracy. Given the backlash and number of connection interfaces in the drivetrain, the realistic positioning accuracy is closer to the +/−50 microliters.

The interface board is the electronics board that produces the output signals that can be read by external hardware to monitor, and syncopate with, the actions of the pump. The delivered signals are available through the BNC connections on the rear of the pump. The trigger pulse is a TTL level pulse that is delivered every time the trigger code indicates a detected Q-wave. This connection requires a terminated impedance of at least 75 Ohms. The piston position is a 12-bit analog voltage output that spans 0-5 VDC. It is proportionally related to the full travel of the piston, with zero volts equating to the piston completely empty. The ECG output is also an analog voltage output of the same range and precision as the piston pump. It is the direct recreation of the ECG board Lead II output, with a sample delay of ~5 milliseconds. The Piston Position and ECG Output BNC connections should be terminated with an impedance of at least 330 Ohms.

The pump has two power supplies to support the motor drive and the electronics in the pump. The motor drive supply is a 48V 4A DC unit. It is a closed frame design and is mounted underneath the drivetrain. The electronics power supply is a 5V and 12V DC output. It is an open frame design that is mounted to the back panel and is located underneath the electronics mounting plate. The electronics supply is directly connected to the cooling units on the pump through the Sensor Shield. Once power is delivered to the unit, the cooling units should turn on. Both power supplies connect to the same fused power entry port that is mounted on the back panel of the pump. The fuse box is accessible just above the power cable connection on the outside of the unit.

The control code architecture uses discrete operating states to perform the requisite action of the pump in the prescribed states of use: priming, pause/idle, pump with trigger, and pump without trigger. In one embodiment, the operating code is organized into nested subsystems. When the embedded code is generated to conformal ANSI C, without optimizations, the subsystems are embodied as functions. The signals entering the subsystem are input variables in C and the signals leaving are returned values in C. Thus, the compartmentalization of the code follows the functional grouping that would be embodied in a non-model-based design development environment.

Figure 19:
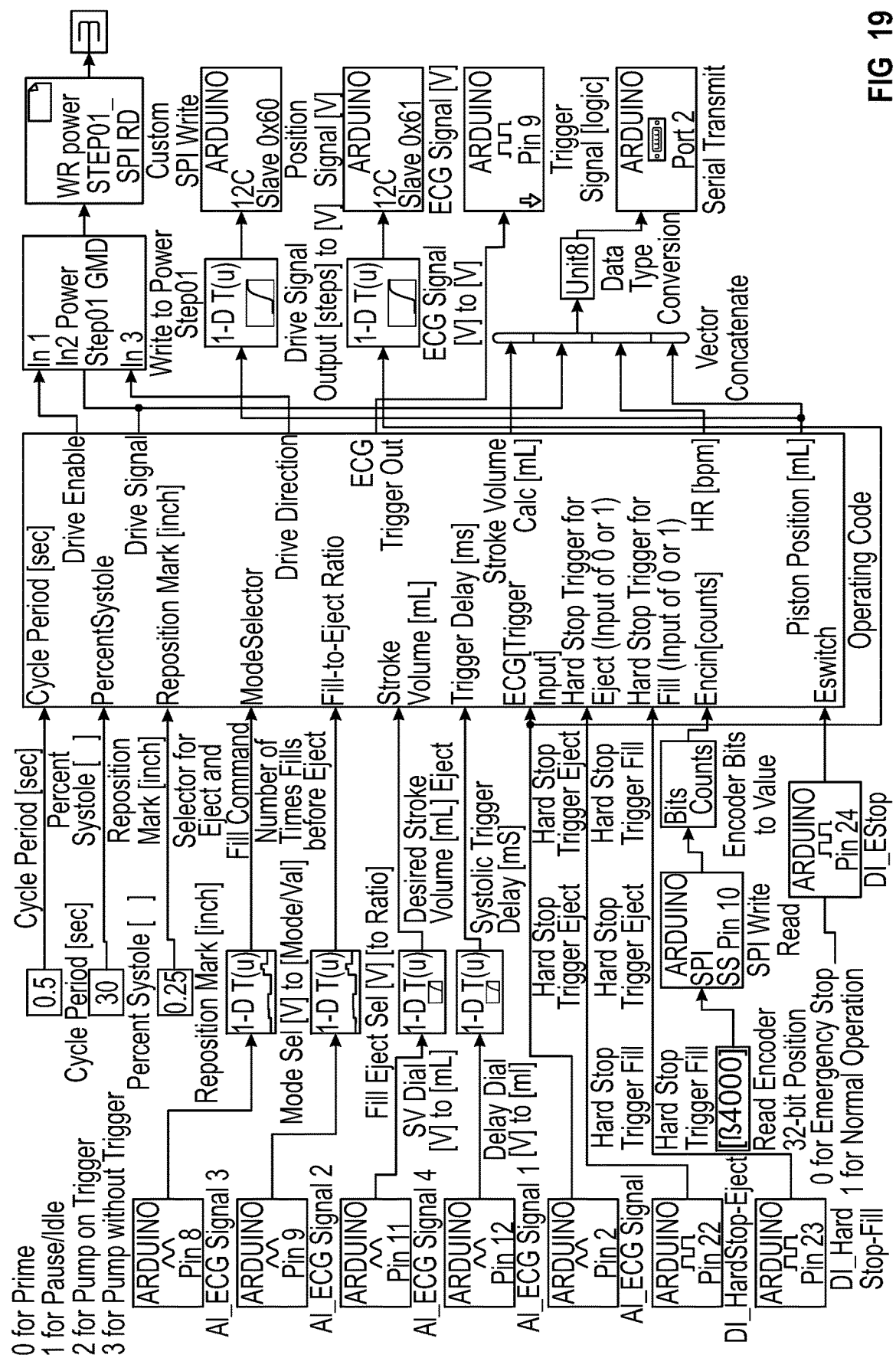
FIG. 19 provides the preferred embodiment of the deployment model utilizing the Atmega 2560 microcontroller in the Arduino Mega 2560 R3 package.

FIG. 19 provides the deployment model, which is used to generate the target-specific code for the Atmega 2560 processor in the Arduino Mega 2560 R3 package. The inputs for the operating code take the form of global settings, hardware readbacks (analog voltage and digital logic), and serial communication (SPI). When processed, these provide the control code input values that govern the chosen operating state function and monitoring of performance. The returned values from the control code are directed to the appropriate outputs: motion controller command, interface board signals, and serial transmit stream.

The operating code is comprised of five subsystems (see FIG. 20): ECG trigger, position encoder processing, operating controls, overwrite and error control, and readback processing. The ECG trigger subsystem is the code shown in FIG. 1. The position encoder processing assembles the bytes returned from the counter monitoring the quadrature encoder on the actuator, and produces the drawn volume of the piston in milliliters. The operating controls is the central processing of the action to be taken by the system. The overwrite and error control works to ensure safe operation of the pump through the monitoring of the hardware limit switches and operating conditions of the system (e.g. pump rate, ECG trigger loss). The readback processing subsystem is tasked with monitoring the operating conditions and providing performance metrics (e.g. heart rate from the ECG signal). The goal of the operating code is to process the desired settings from the interfaces on the rear of the unit, execute intended action, and monitor system conditions to ensure safety. This is returned as commands to the motion controller, interface signals to external systems and a serial stream to a monitoring computer.

Figure 20A:
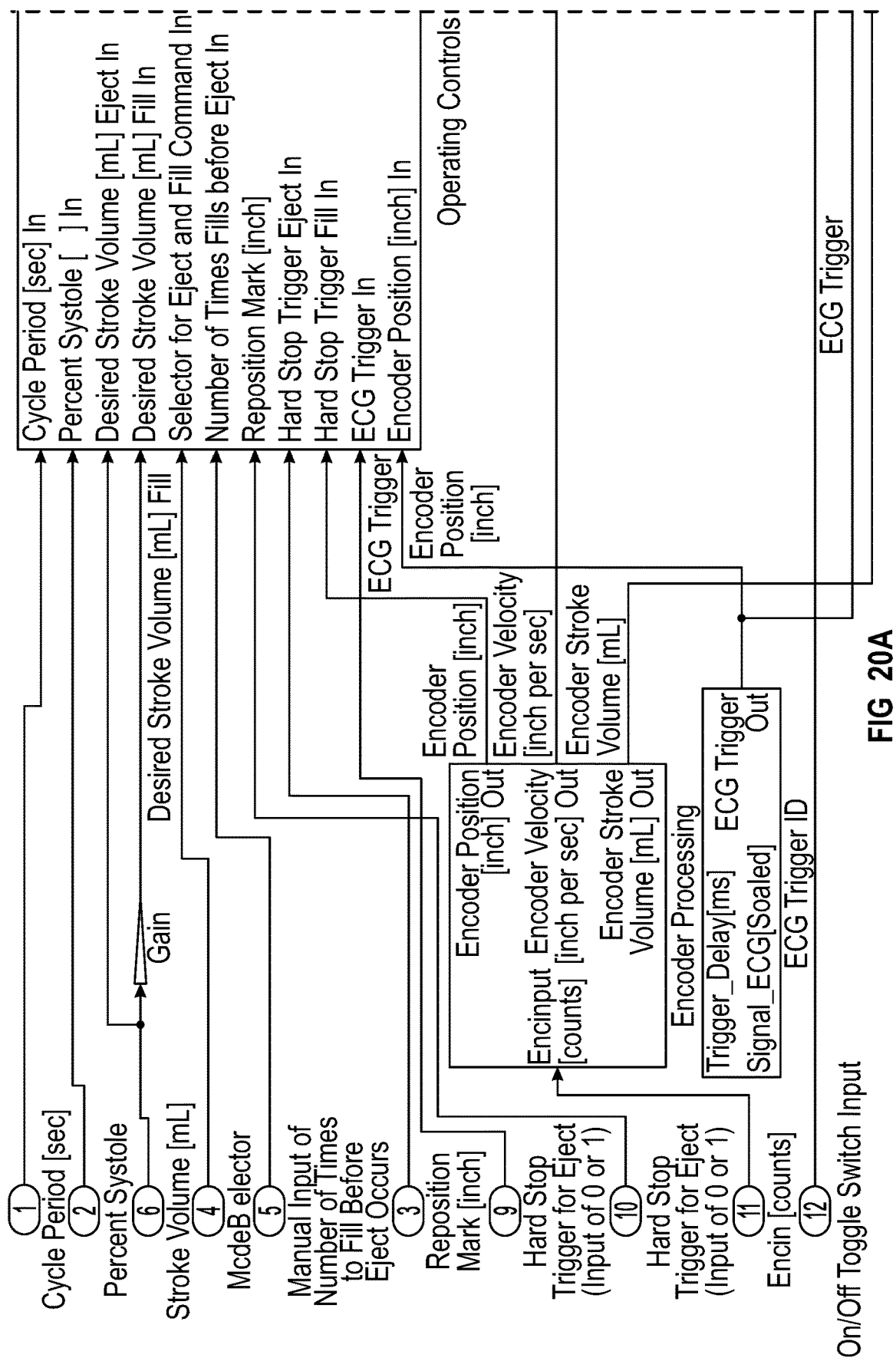
FIGS. 20A and 20B together provide a diagram of the operating code, comprising five subsystems: ECG trigger, position encoder processing, operating controls, overwrite and error control, and readback processing.
Figure 20B:
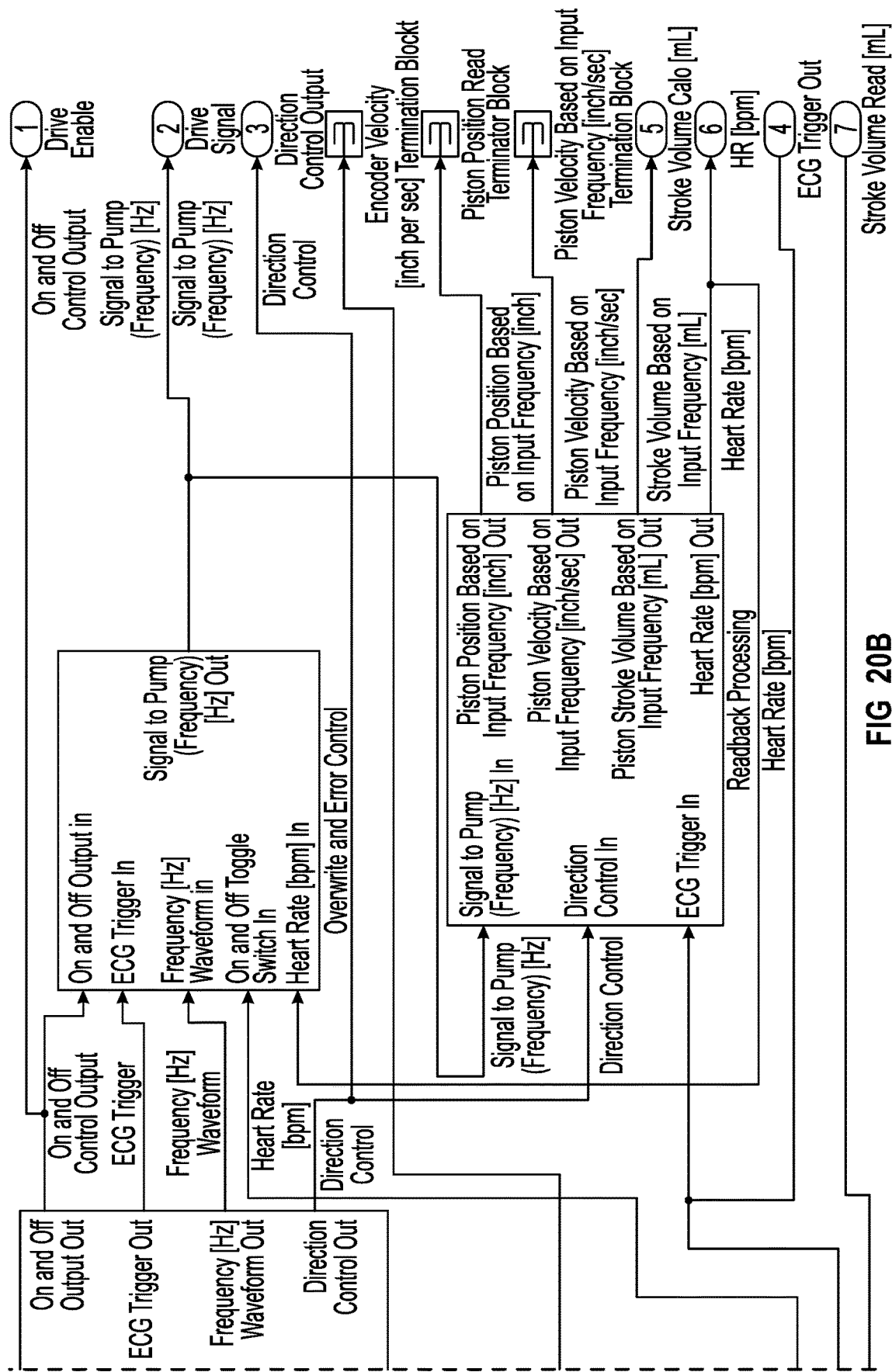

The inputs to the operating ode are seen on the left side of the model shown in FIG. 20. These can originate from simulated signals for a computational analysis or physical signals taken from hardware on an embedded target. The Encoder Processing and ECG Trigger ID process the signals that would originate from the quadrature encoder counter IC and the EKG shield, respectively. The Operating Controls subsystem integrates the sensor signals and the ECG trigger information into motion commands for the actuator. The Overwrite and Error Control subsystem monitors the action of the systems to prevent possible failure states. The Readback Processing subsystem calculates metrics on the system that are used to monitor system function for safety and documentation. Signals returned from the code are connected to numbered ports, signals ending in a termination block are not.

Figure 21A:
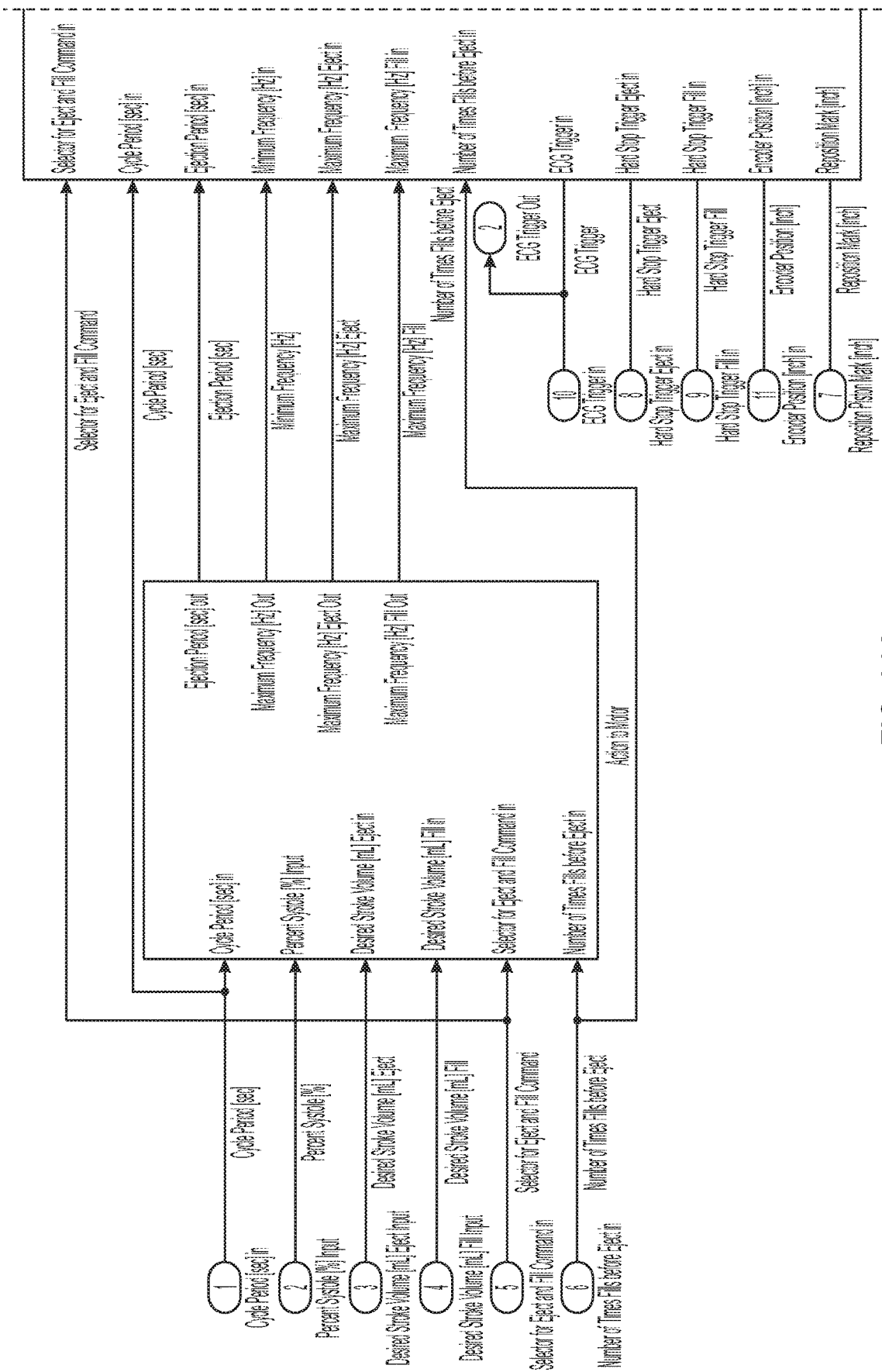
FIGS. 21A and 21B together provide a diagram of the operating controls subsystem code.
Figure 21B:
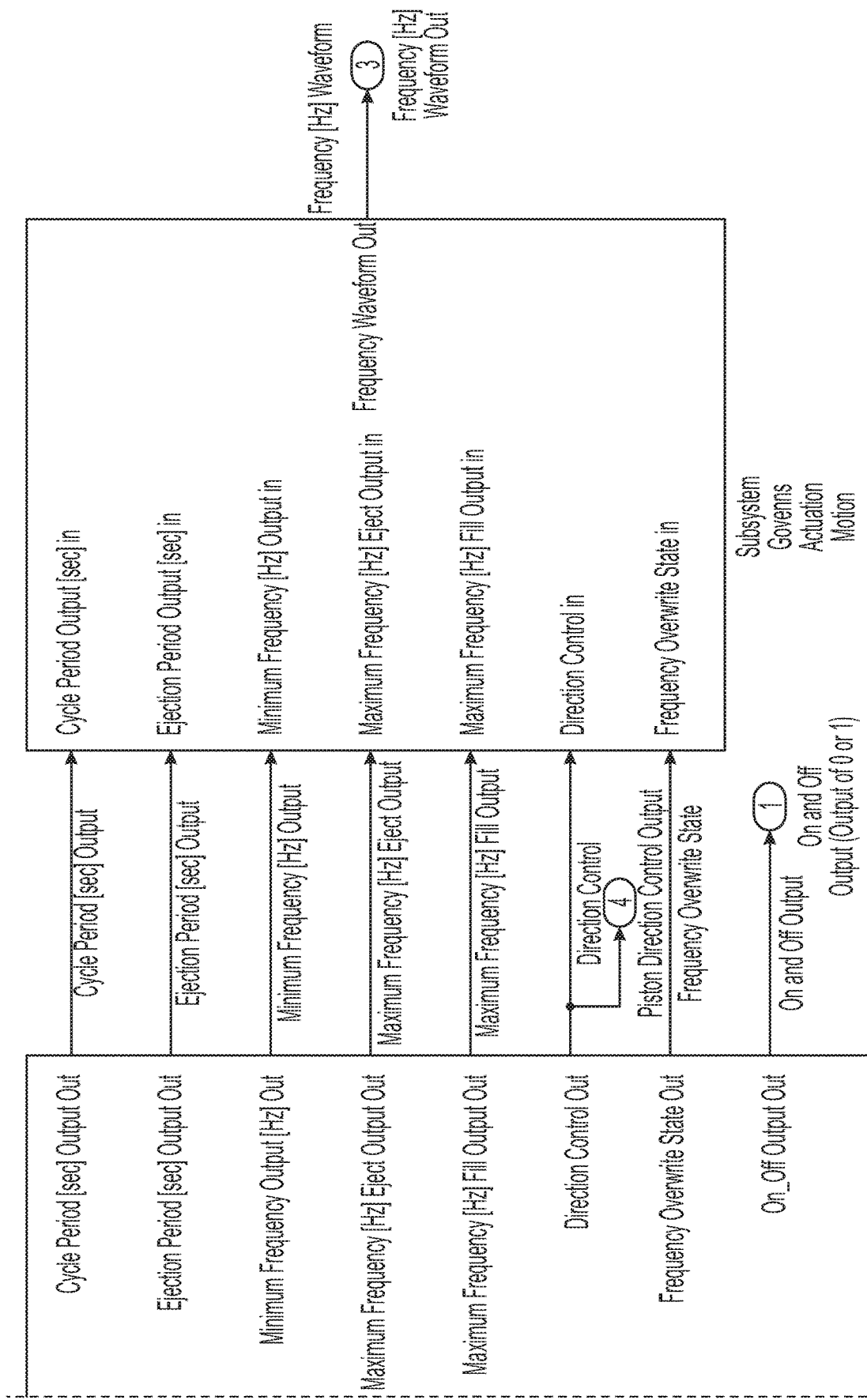

As seen in FIG. 21, the Operating Controls subsystem code is grouped into three seconds: Action to Motor, Operating States Table, and Subsystem Governs Actuation Motion. The Action to Motor determines the timing and magnitude characteristics of the motion profile, which are connected to the hardware configuration of the pump (e.g., piston size, actuator being used). The Operating States table integrates timing values with the trigger signal and intended operating mode of the pump. Governs Actuation Motion develops the velocity profile to be taken by the piston (e.g. sinusoidal, square) during a pumping cycle and produces the motion command in the form a Frequency Waveform value that is proportional to the intended velocity of the piston at a given time point. The main return information for this subsystem is: enable motion logical value, direction of piston motion, velocity of piston.

The Operating Code subsystem Operating Controls performs the main calculations that govern the action of the pump. This section of code is compartmentalized to connect the pump function with the geometry of the piston (Action to Motor), action to be taken (Operating States Table), and velocity profile (Govern Actuation Motion). The geometry of the piston significantly impacts the limits of operation for the pump; the larger the piston the slower the maximum achievable speed due to friction of the O-ring seal.

The code is not easily configurable to different pump head geometries. The values associated with the pump head need to be hard-coded into both Action to Motor and Governs Action Motion subsystems, with the resulting code generated for the specific embodiment of the pump hardware.

The Operating States Table has four primary states governing the function of the pump. These are defined as: Prime, Pause/Idle, Pump on Trigger, and Pump without Trigger. Prime causes the pump to fill and eject at the prescribed stroke volume set on the interface dial at a period of 0.5 Hz, a slow sequence that runs indefinitely. The Pause/Idle state holds the pump at the stroke volume position set on the Stroke Volume dial. This can be a temporary state used to hold a volume in the piston for a period of time before returning to a pumping state. Moving the Stroke Volume dial in this operating state will cause the piston to move to that draw volume. The Pump on Trigger state ejects the column in the cylinder when the prescribed delay from the Delay Dial has been completed after the ECG Trigger signal changes states (indicating a Q-wave).

After the eject sequence, the fill sequence ensues with the prescribed number of fill steps per ejection being determined by the Fill:Eject Ratio Selector position on the rear panel. If the ratio is not 1:1, the pump performs a prescribed number of fills prior to ejecting the target volume.

The fill sequence always occurs after the allotted time for the ejection sequence, which follows the delay from the Q-wave. The period of pumping, ejection and fill periods, is a fixed 0.5 seconds. The ratio of ejection time to total cycle (eject+fill time) is 30%. Thus, the ejection period is always 150 milliseconds and the fill period is always 350 milliseconds. Changes to the periods of action are hard coded and are connected to the geometry of the hardware; shorter time periods results in higher calculated speeds of the piston that may violate the operational limits of the actuator.

Future embodiments of the pump could include measurement of pressure at a variety of points in the hydraulic system. This information could be integrated into the pump control to provide pressure controlled filling and ejection pressure measurement. This functionality could be integrated with monitoring of the physiological system to ensure that the pump function was not adversely impacting the state of the organism.

The final state of Pump without Trigger is similar to the previously discussed state, without the ejection waiting for the ECG trigger. The delay settings provide a delay between the conclusion of a fill and the commencement of an eject sequence. The ratio of fill to eject functionality is preserved. This state is useful when seeking to operate the pump without an ECG trace to determine hydraulic performance of a connected fluid system under a variety of pumping states.

Figure 22:
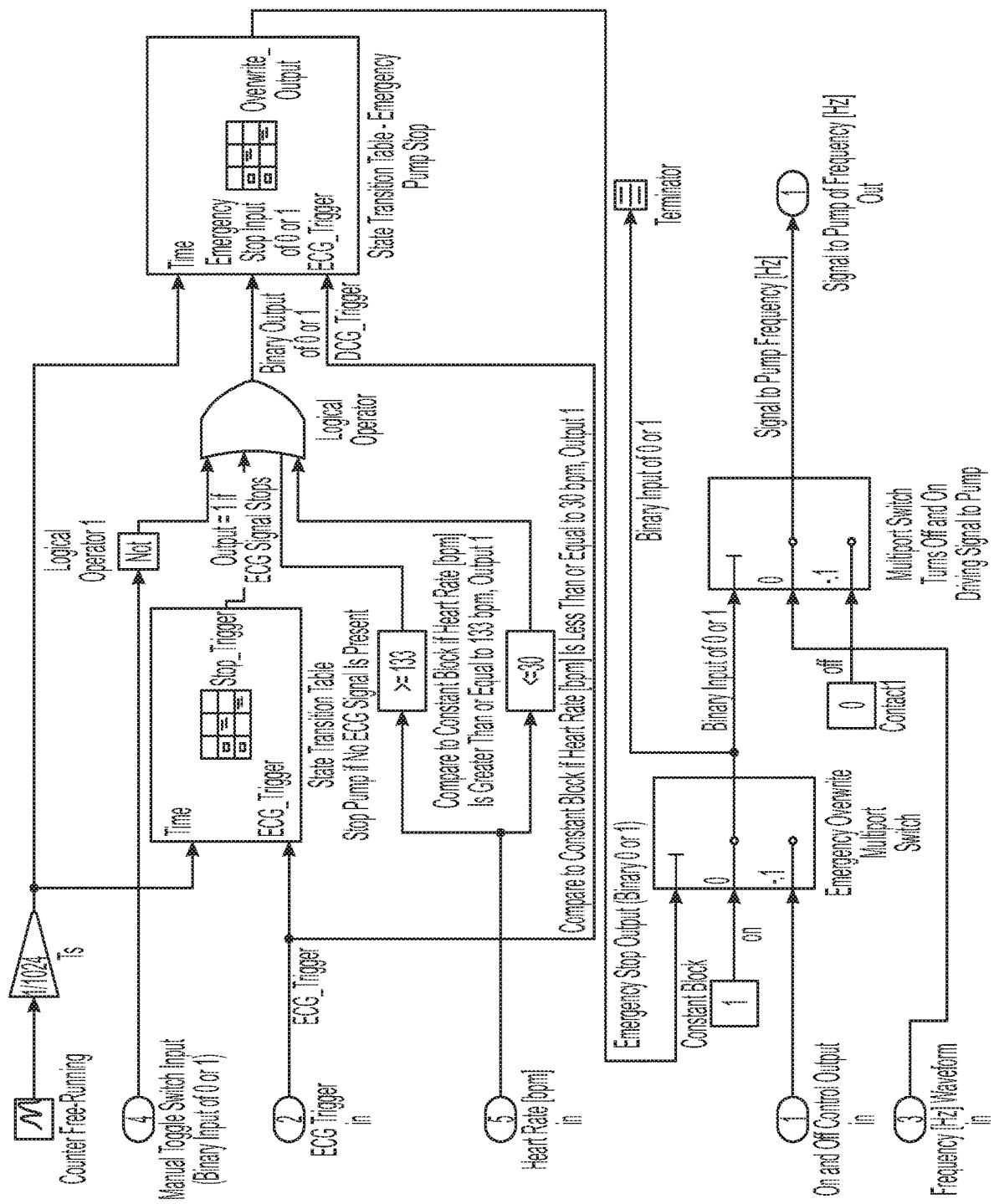
FIG. 22 provides the logic diagram of the overwrite and error control subsystem. The state transition table "Stop If No ECG Trigger" monitors the ECG Trigger signal and produces a stop command if the trigger is absent for 3 seconds, this will be reset once the trigger returns. The HR limits for the pump, determined by the ECG signal measurements are 30 and 120 BPM, values outside this range stop the pump. The Emergency Stop table introduces a refractory period of 30 seconds after a stop event, and waits for 10 seconds of ECG trigger before resuming. This subsystem is bypassed for all states other than the Pump with Trigger mode.
Figures 23, 24A:
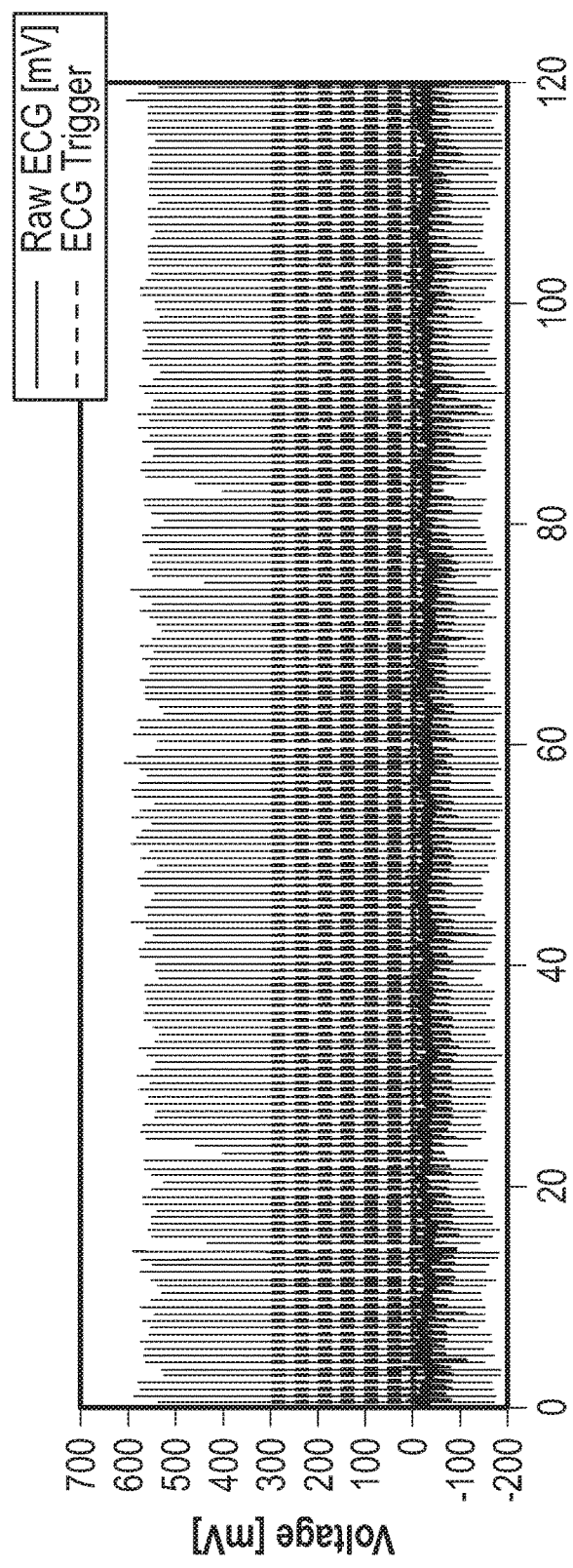
FIG. 23 provides a table of the results of the parametric analysis studies to determine pump ejection based on ECG Events.
FIG. 24(a) provides the recorded signals showing the pump action with variance in the cycle period, wherein the graph provides the voltage measurement for the Raw ECG and the ECG trigger over time.
Figure 26C:
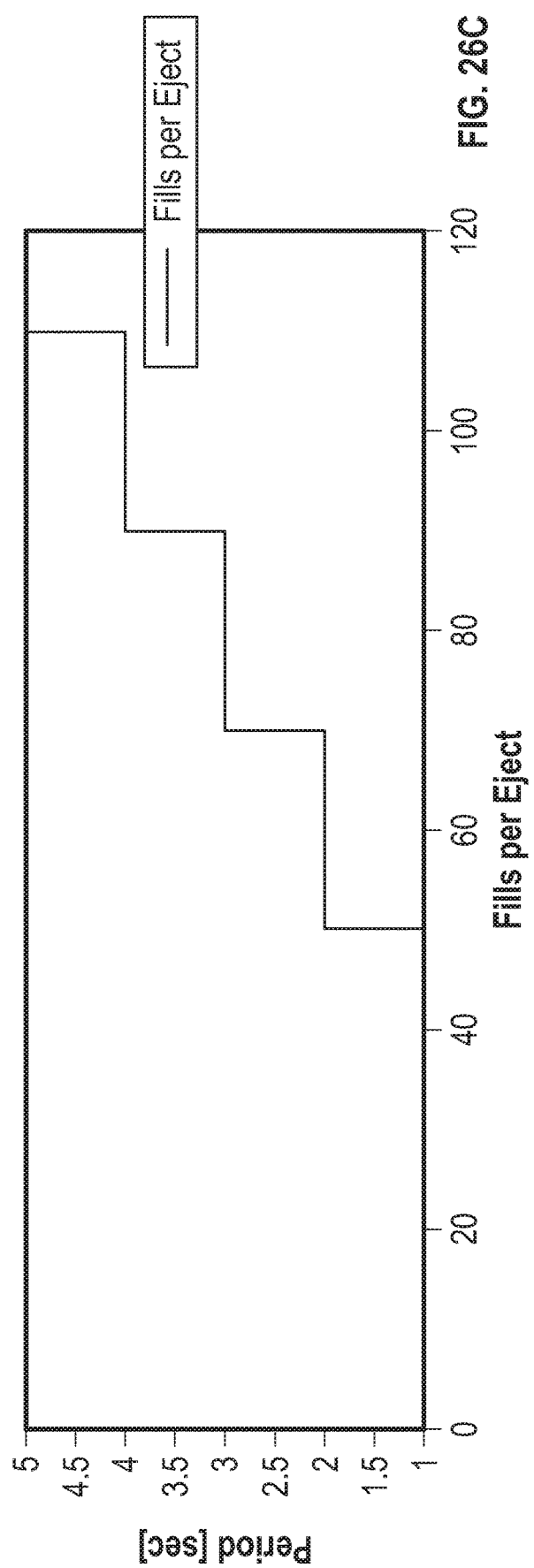
FIG. 26(c) provides a focused plot of the signals for cycle period results for the 0.30 second cycle period segment at the end of the analysis, measuring the cycle period.
Figure 27A:
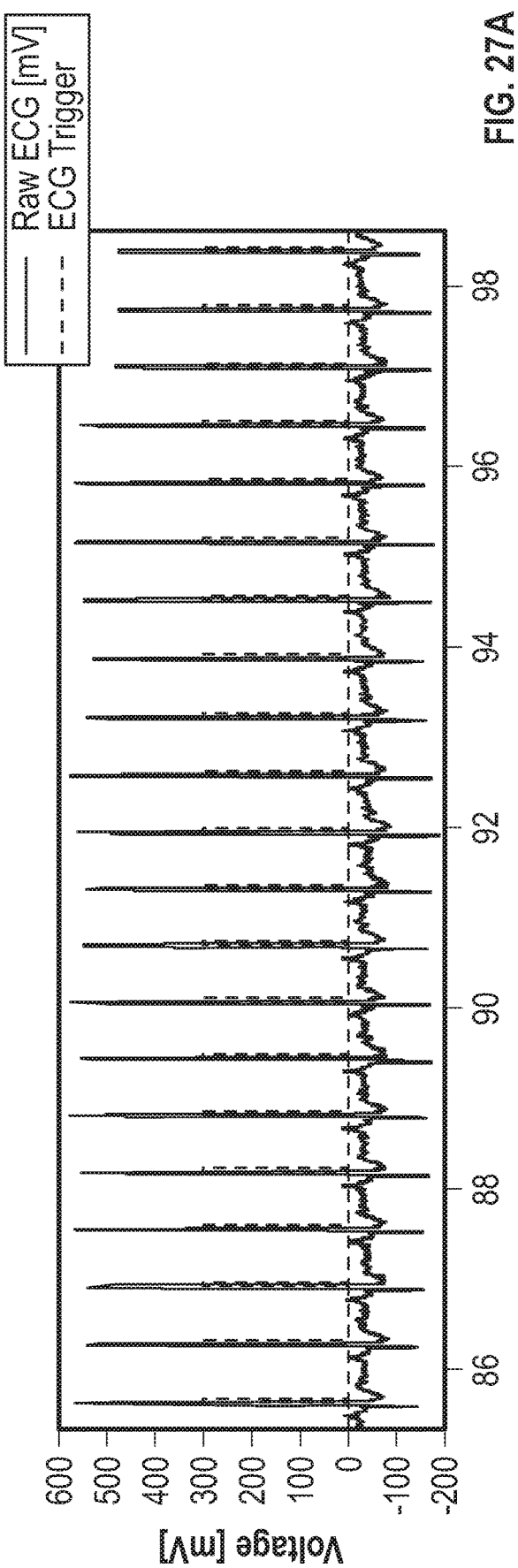
FIG. 27(a) provides the recorded signals highlighting the transition from 3:1 Fills:Eject with the two second stop between setting changes, herein measuring the voltages over time of the Raw ECG and ECG Trigger.
Figure 27B:
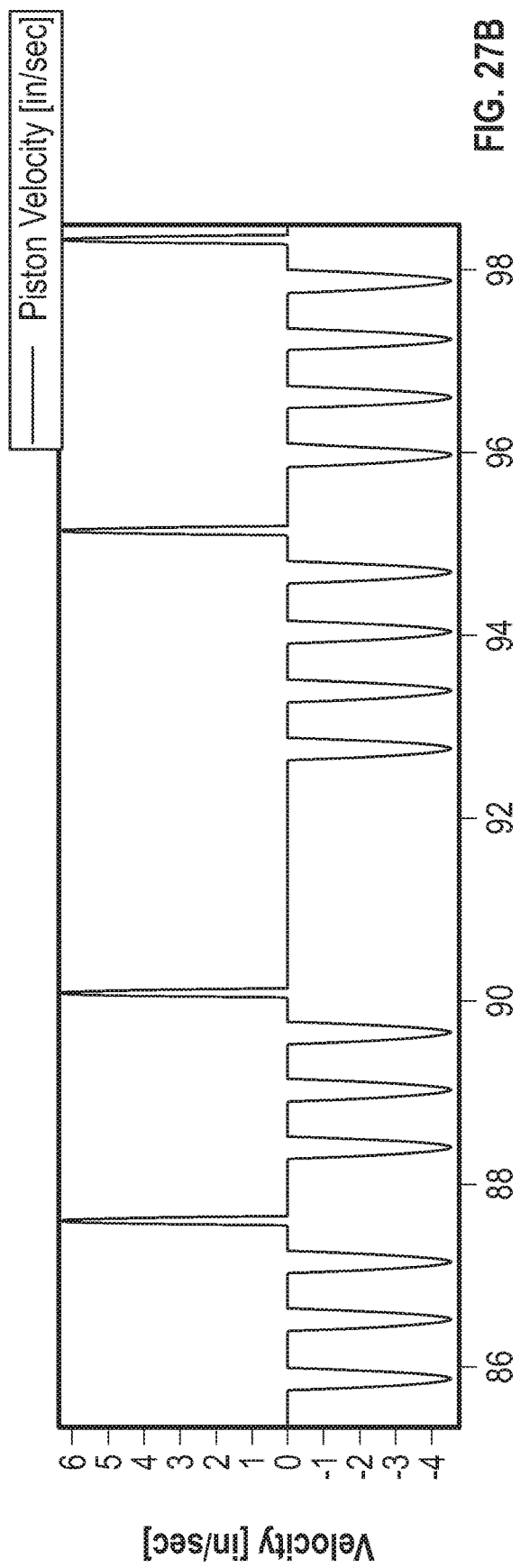
FIG. 27(b) provides the recorded signals highlighting the transition from 3:1 Fills:Eject with the two second stop between setting changes, herein measuring the piston velocity over time.
Figure 27C:
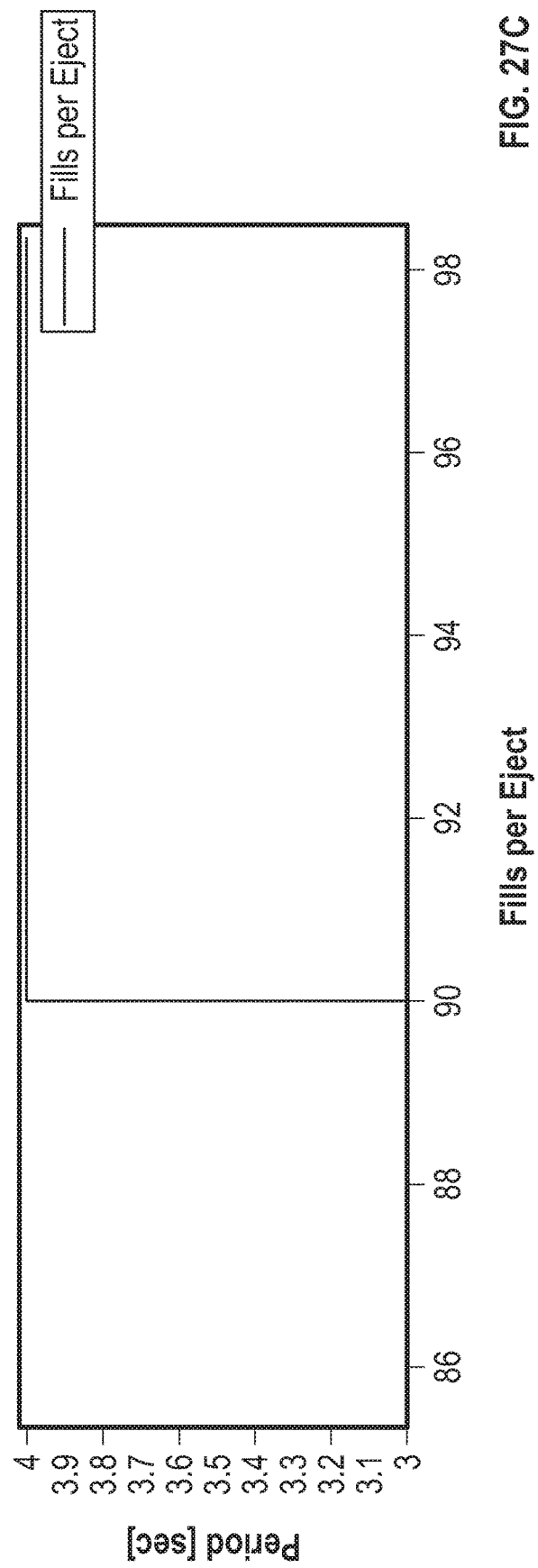
FIG. 27(c) provides the recorded signals highlighting the transition from 3:1 Fills:Eject with the two second stop between setting changes, herein measuring the fills per eject for each cycle period.
Figure 28C:
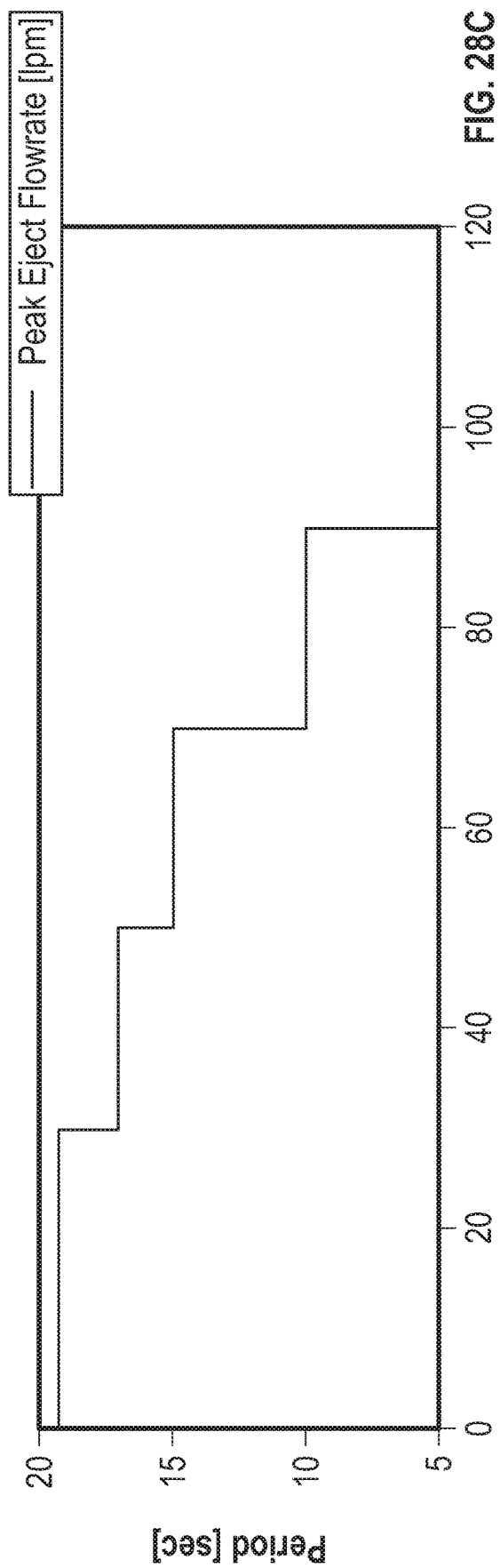
FIG. 28(c) provides the recorded signals showing the change in peak ejection flowrate, which is the calculated runtime variable based on the stroke volume knob selection, wherein the signal measures the peak ejection flowrate for each period.
Figure 29A:
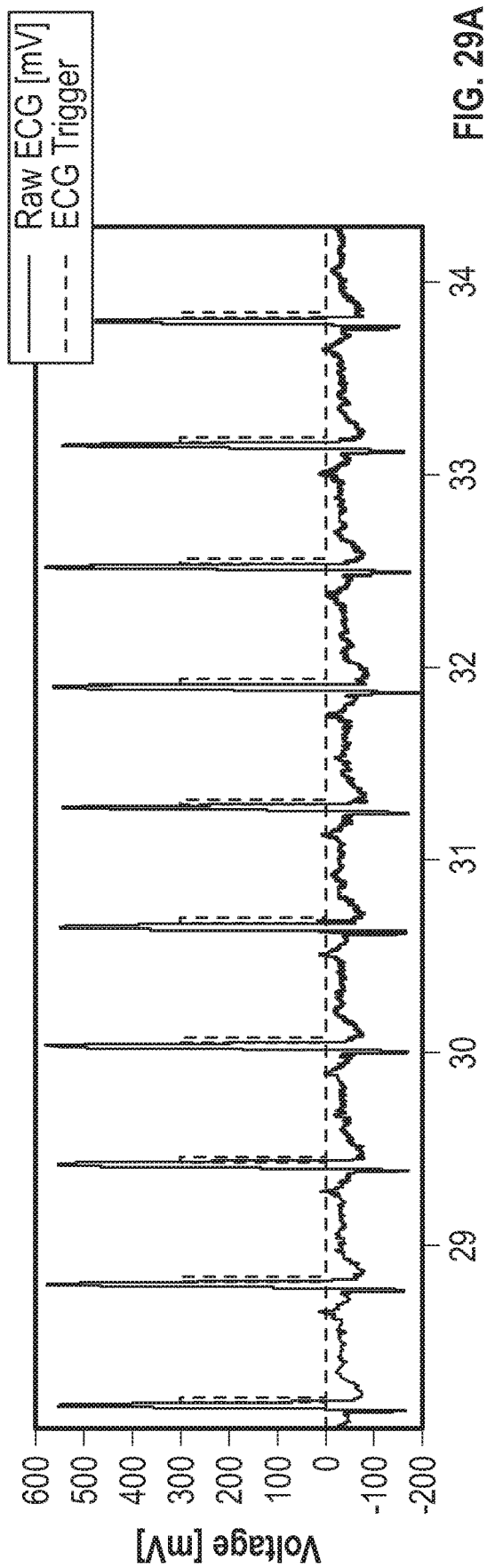
FIG. 29(a) provides the recorded signals that highlight the change in peak ejection flowrate between a settings change, with the programmed pause of two seconds, wherein the signals measured are the voltages of the Raw ECG and the ECG Trigger.
Figure 30A:
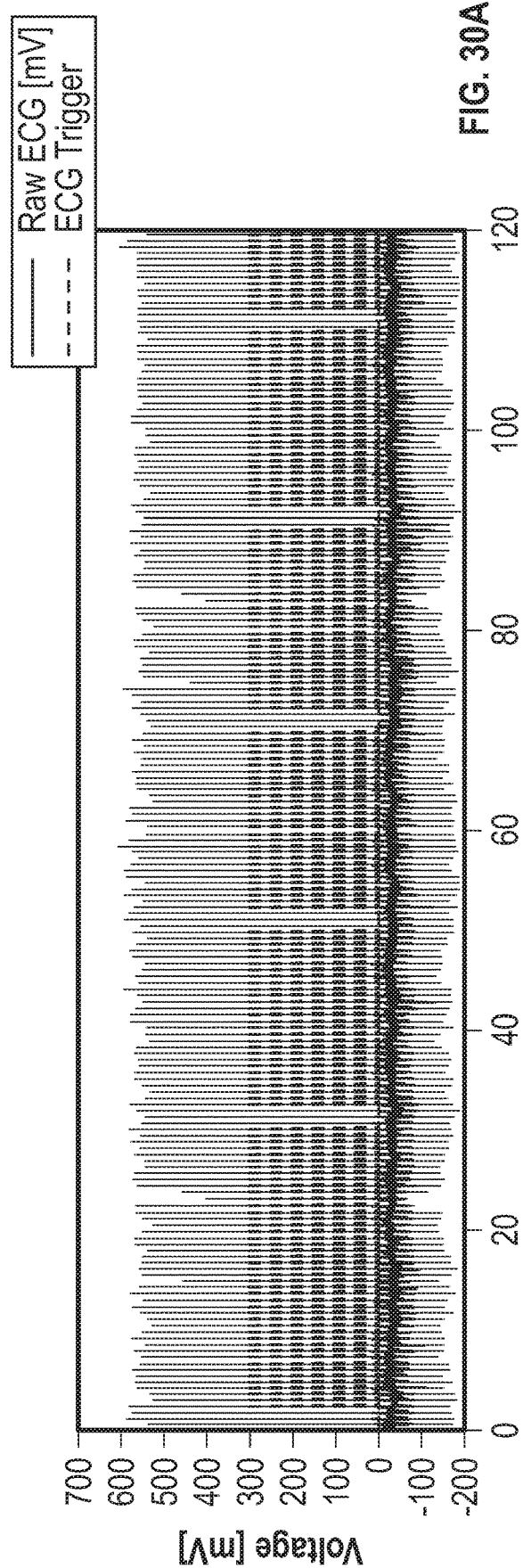
FIG. 30(a) provides the recorded signals for the change in trigger delay from 0 ms to 50 ms. The 0 ms delay has roughly a 1 ms true delay based on the processing of the control code between the q-wave trigger and motion control command. Here, the recorded signals are the voltages of the Raw ECG and the ECG Trigger over time.
Figure 30B:
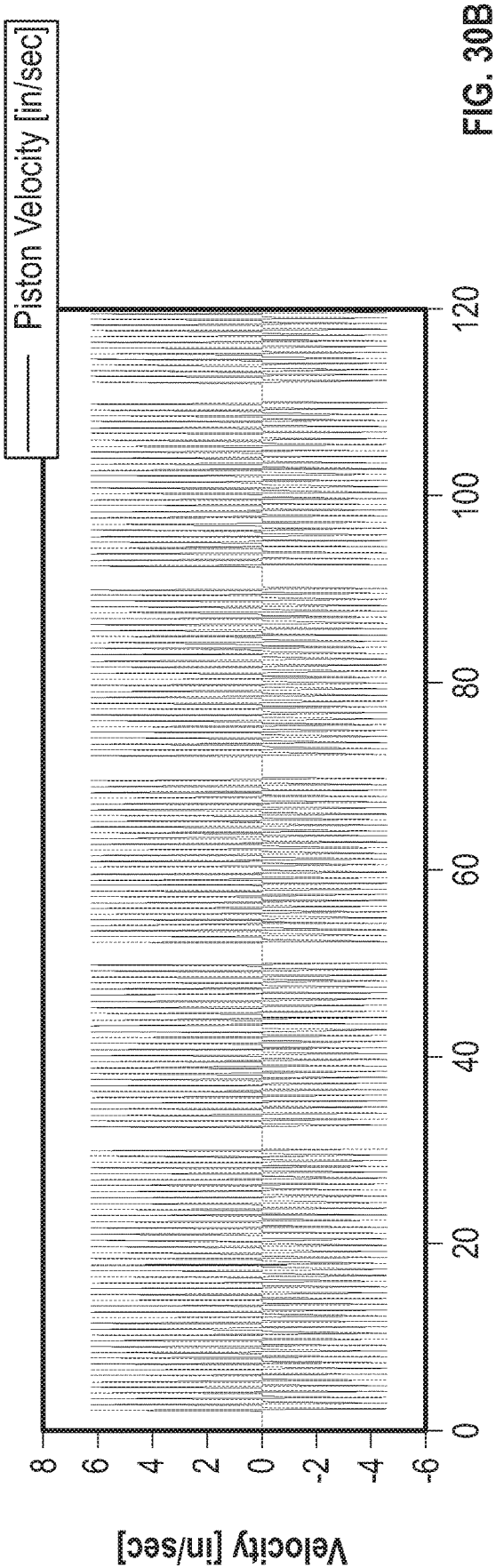
FIG. 30(b) provides the recorded signals for the change in trigger delay from 0 ms to 50 ms. The 0 ms delay has roughly a 1 ms true delay based on the processing of the control code between the q-wave trigger and motion control command Here, the recorded signal is the piston velocity over time.
Figure 30C:
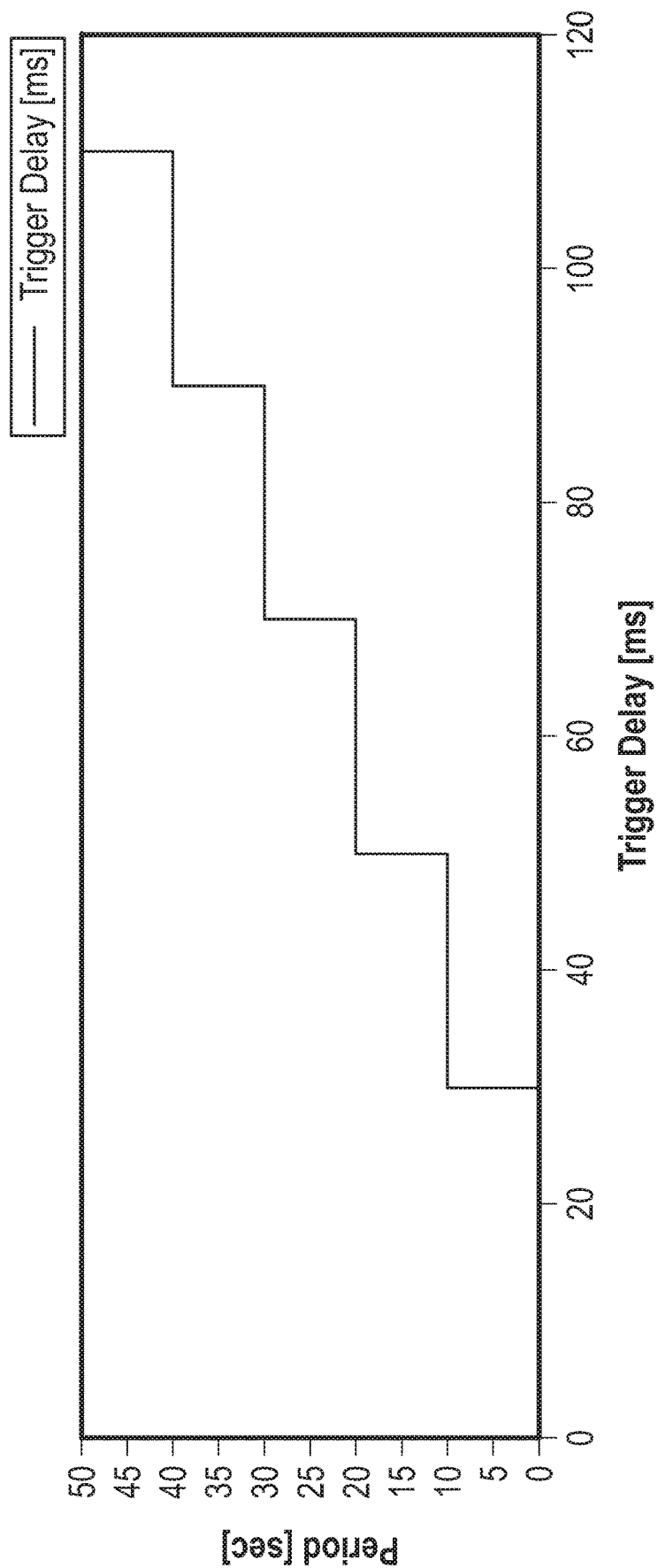
FIG. 30(c) provides the recorded signals for the change in trigger delay from 0 ms to 50 ms. The 0 ms delay has roughly a 1 ms true delay based on the processing of the control code between the q-wave trigger and motion control command Here, the recorded signal is the trigger delay for each period.
Figure 32A:
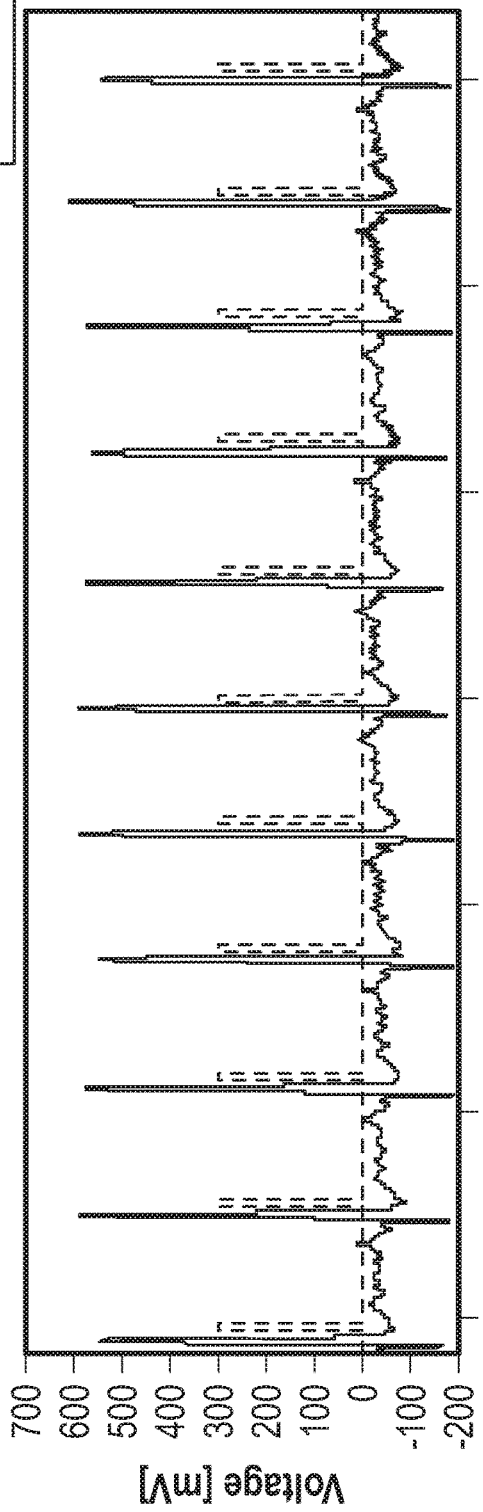
FIG. 32(a) provides the recorded signals of the highlight of the 50 ms delay region illustrating the delay form the QRS complex, wherein the recorded signals are the voltage over time of the Raw ECG and the ECG Trigger.
Figure 32B:
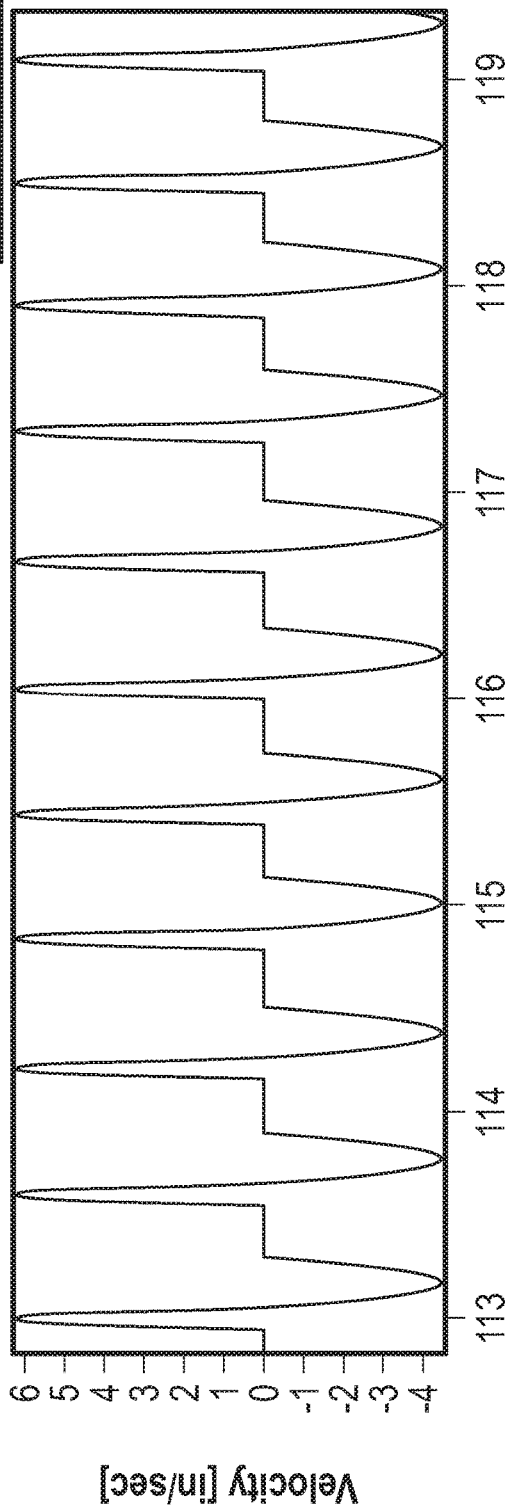
FIG. 32(b) provides the recorded signals of the highlight of the 50 ms delay region illustrating the delay form the QRS complex, wherein the recorded signal is the piston velocity over time.
Figure 33B:
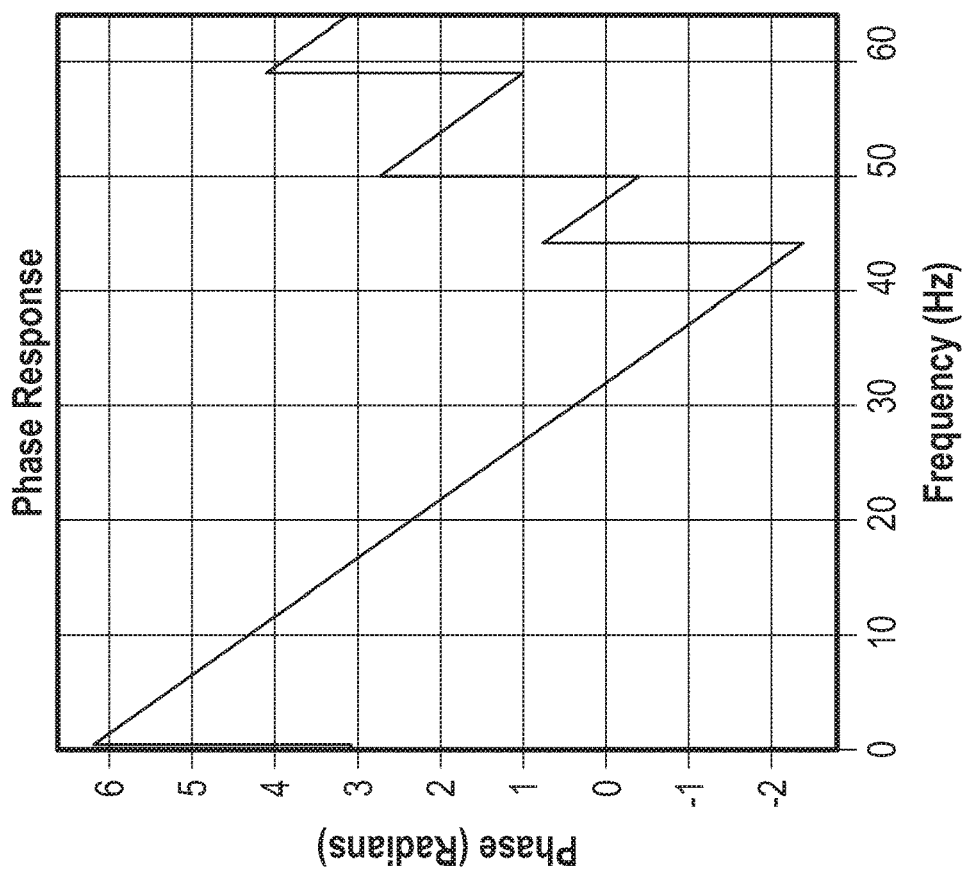
FIG. 33(b) provides the filter design characteristics in a phase plot.
Figure 33A:
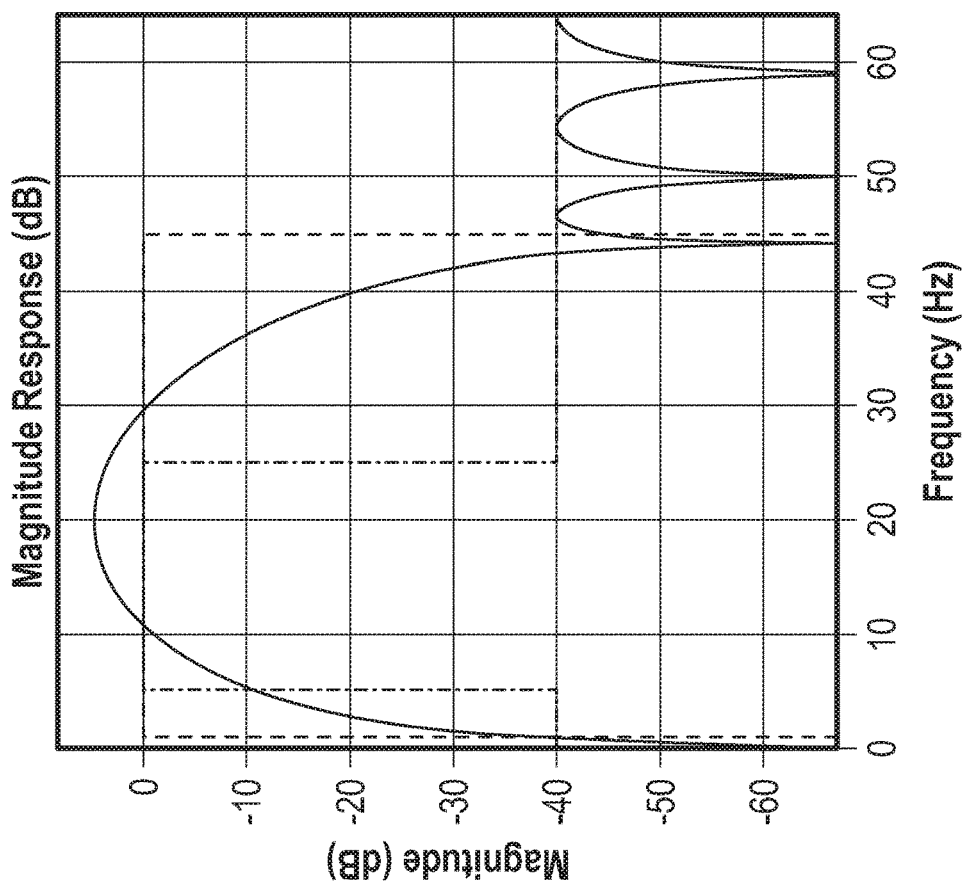
FIG. 33(a) provides the filter design characteristics in a magnitude plot.
Figure 35:
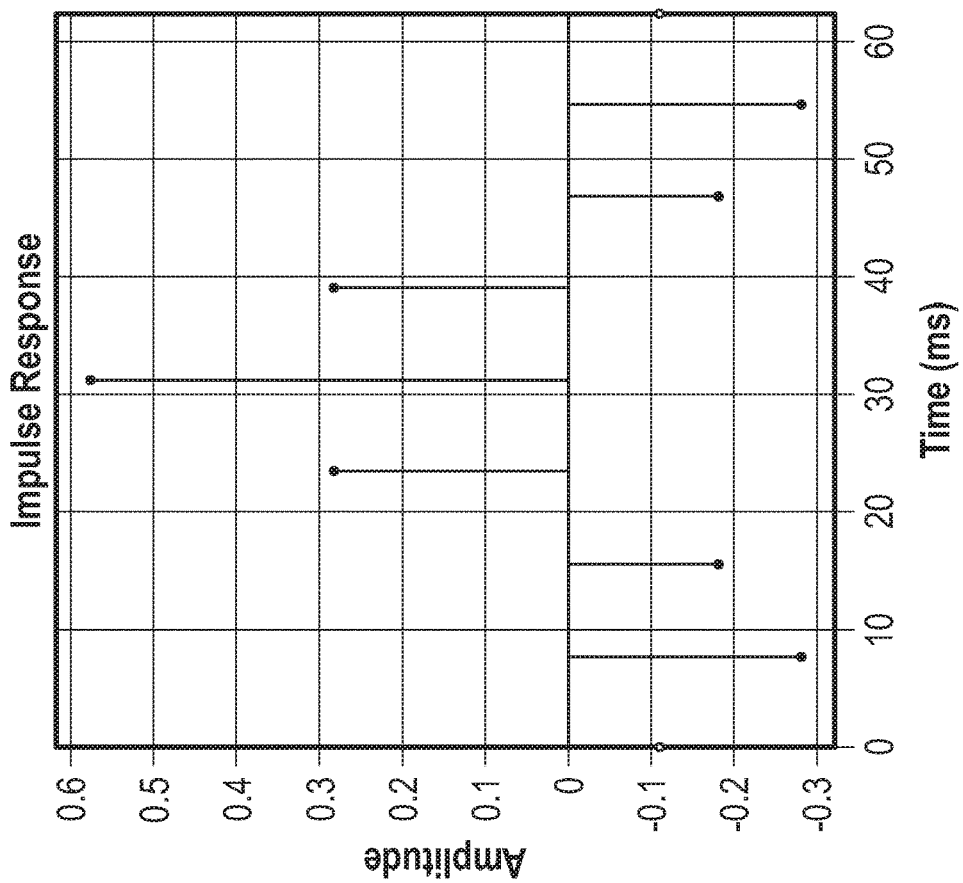
FIG. 35 provides the impulse-response plot for the filter.
Figure 34:
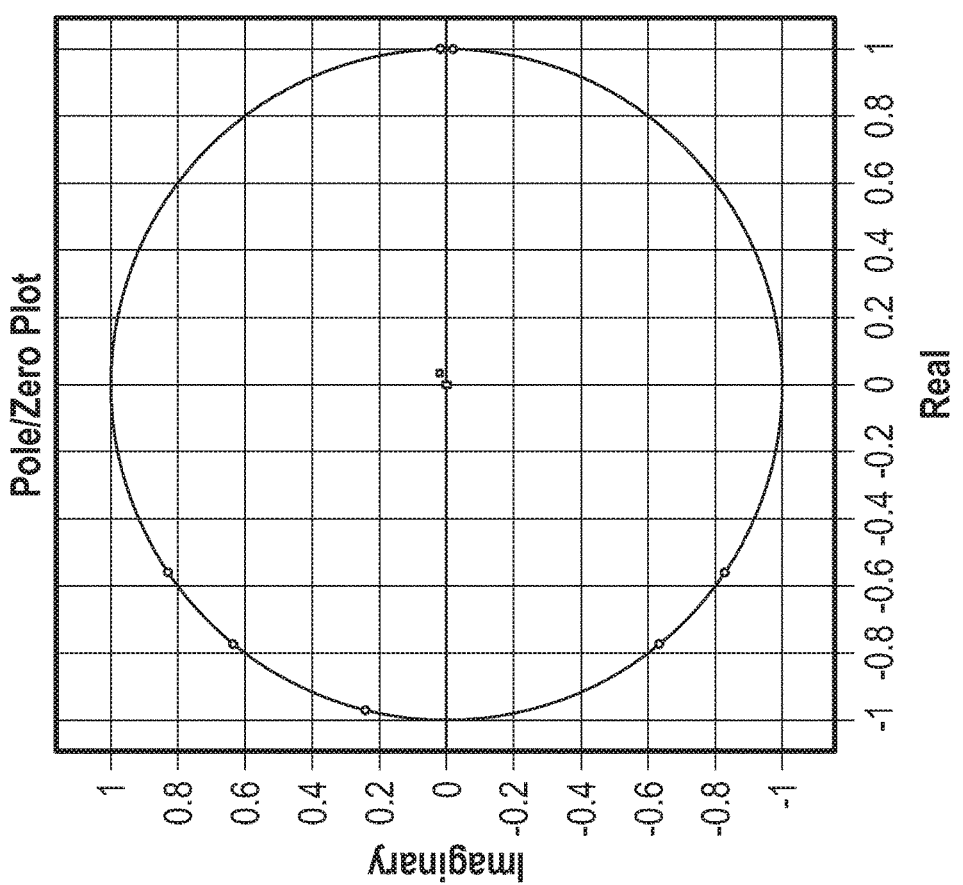
FIG. 34 provides the pole-zero plot for the filter.
Figure 36:
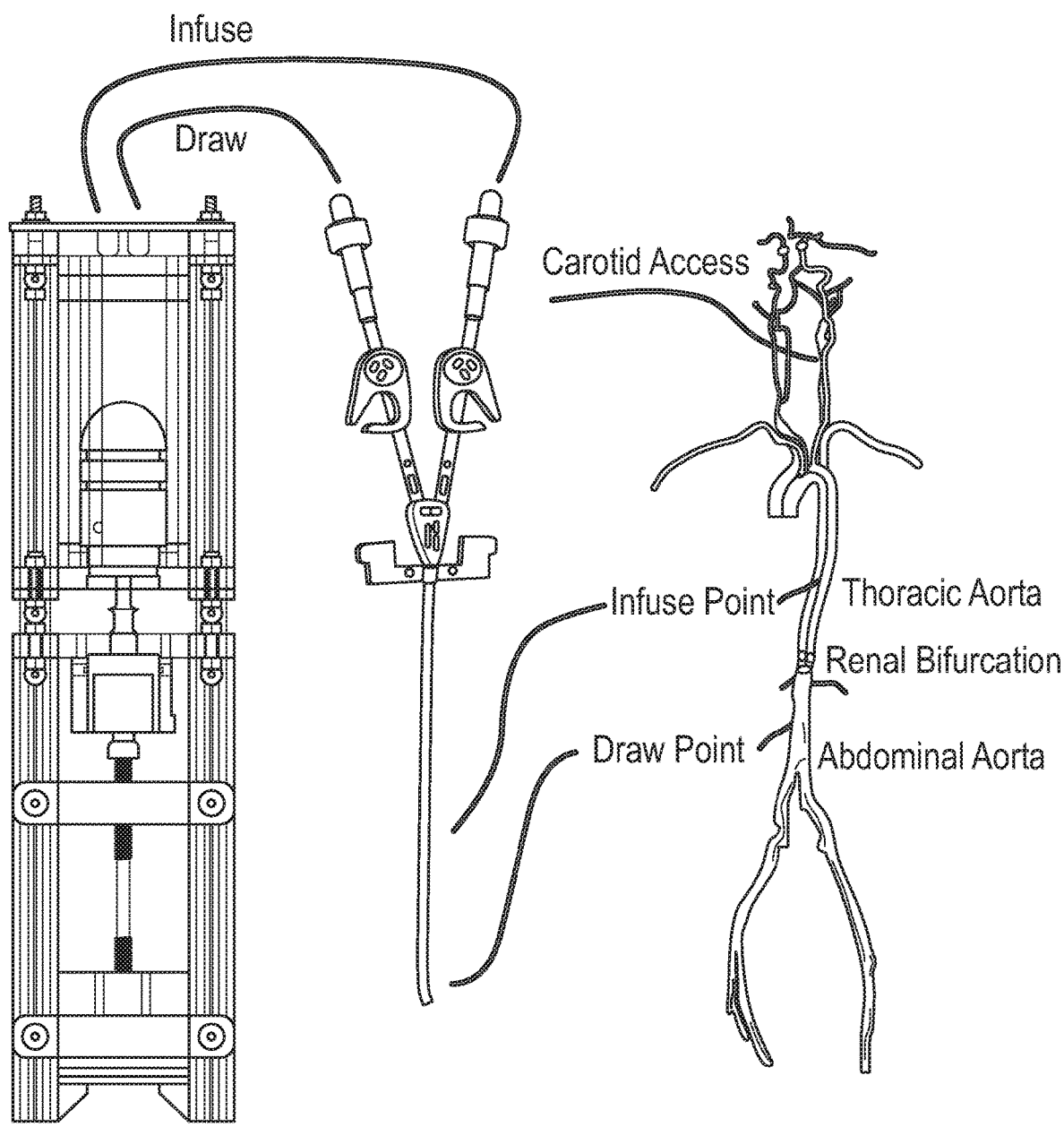
FIG. 36 provides an exemplary connection of the pump to the human systemic arterial tree through the use of a dual-lumen dialysis catheter.
Figure 37:
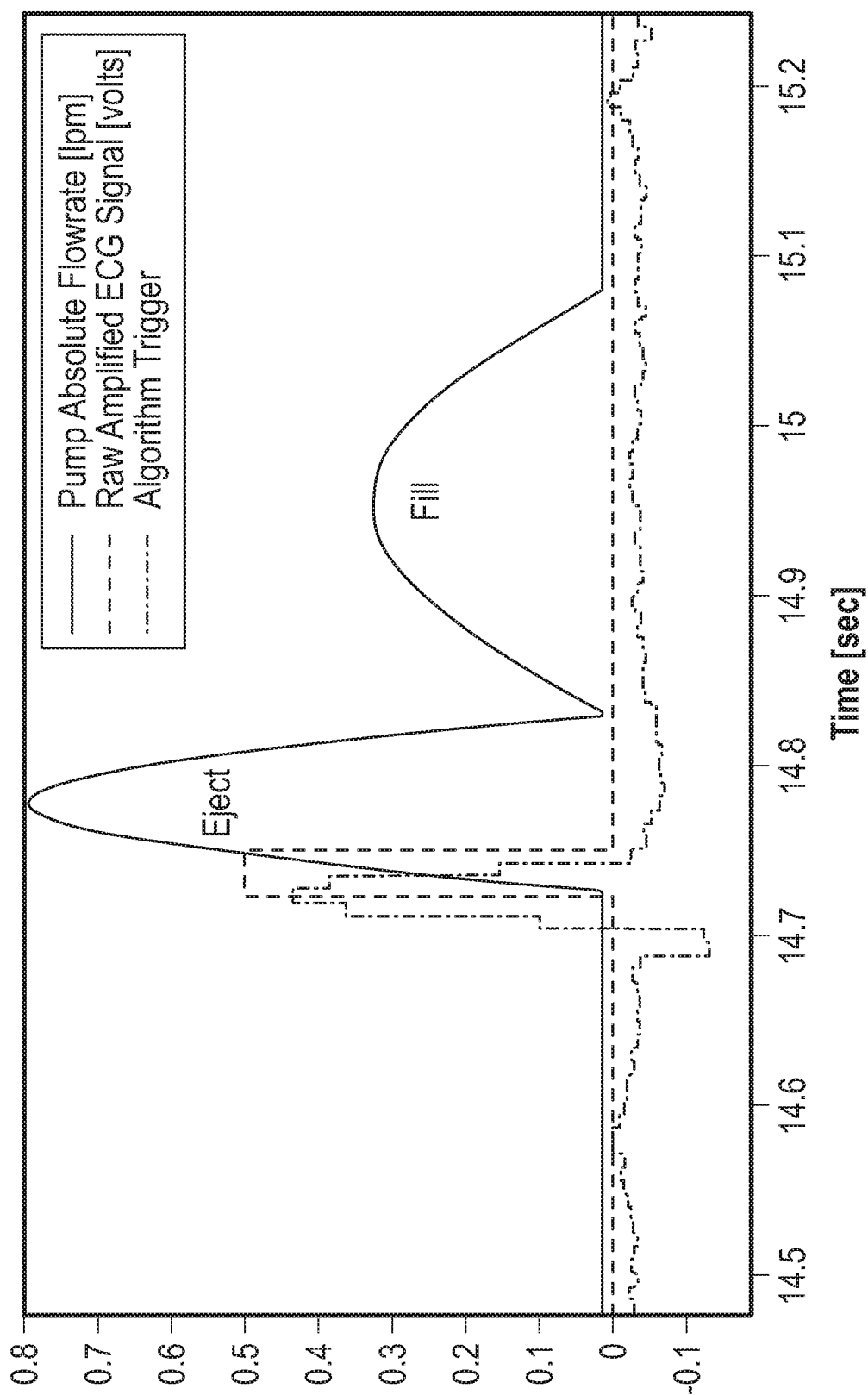
FIG. 37 provides the simulated signal of a 50 mL ejection, 20 ms delay from Q peak, 30% in ejection.

FIG. 22 provides the logic diagram for the Overwrite and Error Control subsystem. The state transition table "Stop If No ECG Trigger" monitors the ECG Trigger signal and produces a stop command if the trigger is absent for 3 seconds. This will be reset once the trigger returns. The HR limits for the pump, determined by the ECG signal measurements are 30 and 120 BPM, values outside this range stop the pump. The Emergency Stop table introduces a refractory period of 30 seconds after a stop event, and waits for 10 seconds of ECG trigger before resuming. This subsystem is bypassed for all states other than the Pump with Trigger mode.

Pump function was examined through parametric analysis of the key values in the code architecture. The goal of this development stage was to determine whether the code architecture can affect changes in the pump action based on settings changes and maintaining triggering action with the ECG signal. Variation in following parameters were chosen to illustrate the appropriate performance on the pump: cycle period, ratio of fills:eject, ejection volume and delay from the Q-wave. The results are presented in FIGS. [24] through [32]. Overall study performance with highlighted regions illustrating the detailed performance. These studies support that the control architecture, particularly the motion profile flexibility, can handle the variance in drive characteristics needed in the application of this prototype.

Figure 12:
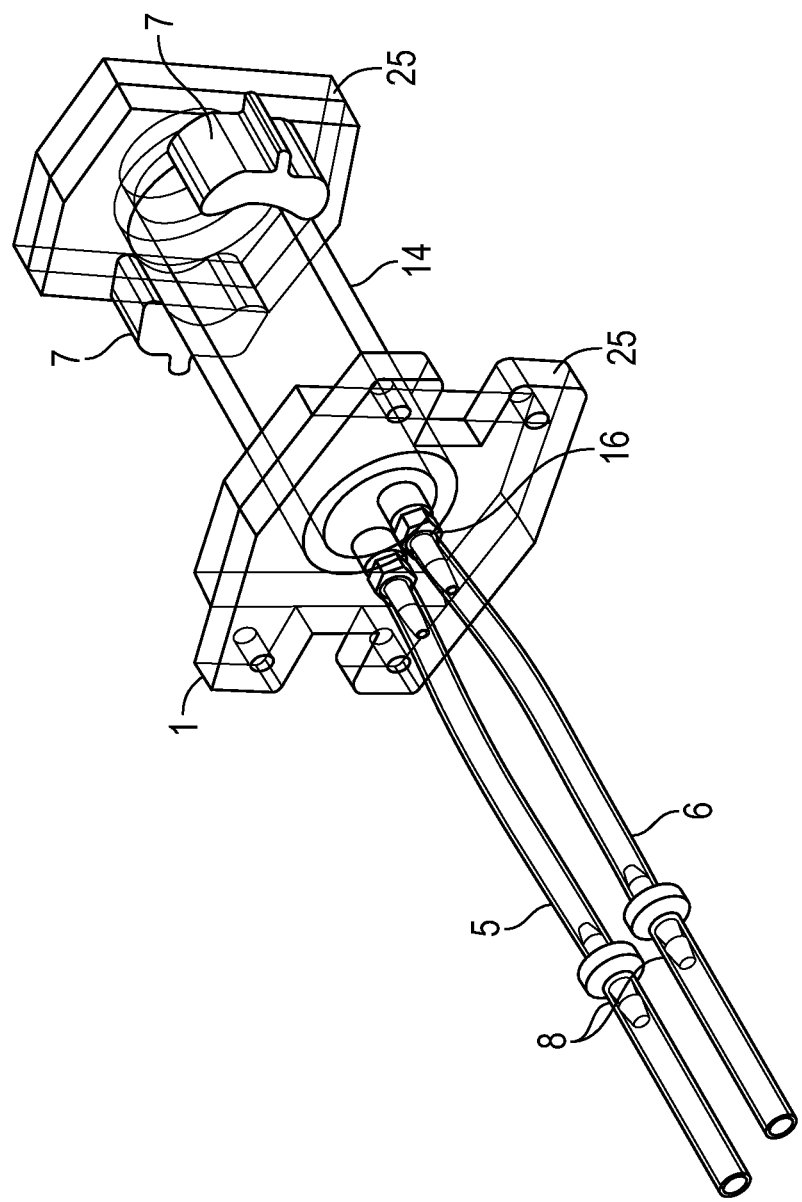
FIG. 12 provides an isolated view of the pump head showing the guide points and mounting face. Tubing, fitting, and check valves are included to show the fluid connections for the design.
Figure 13:
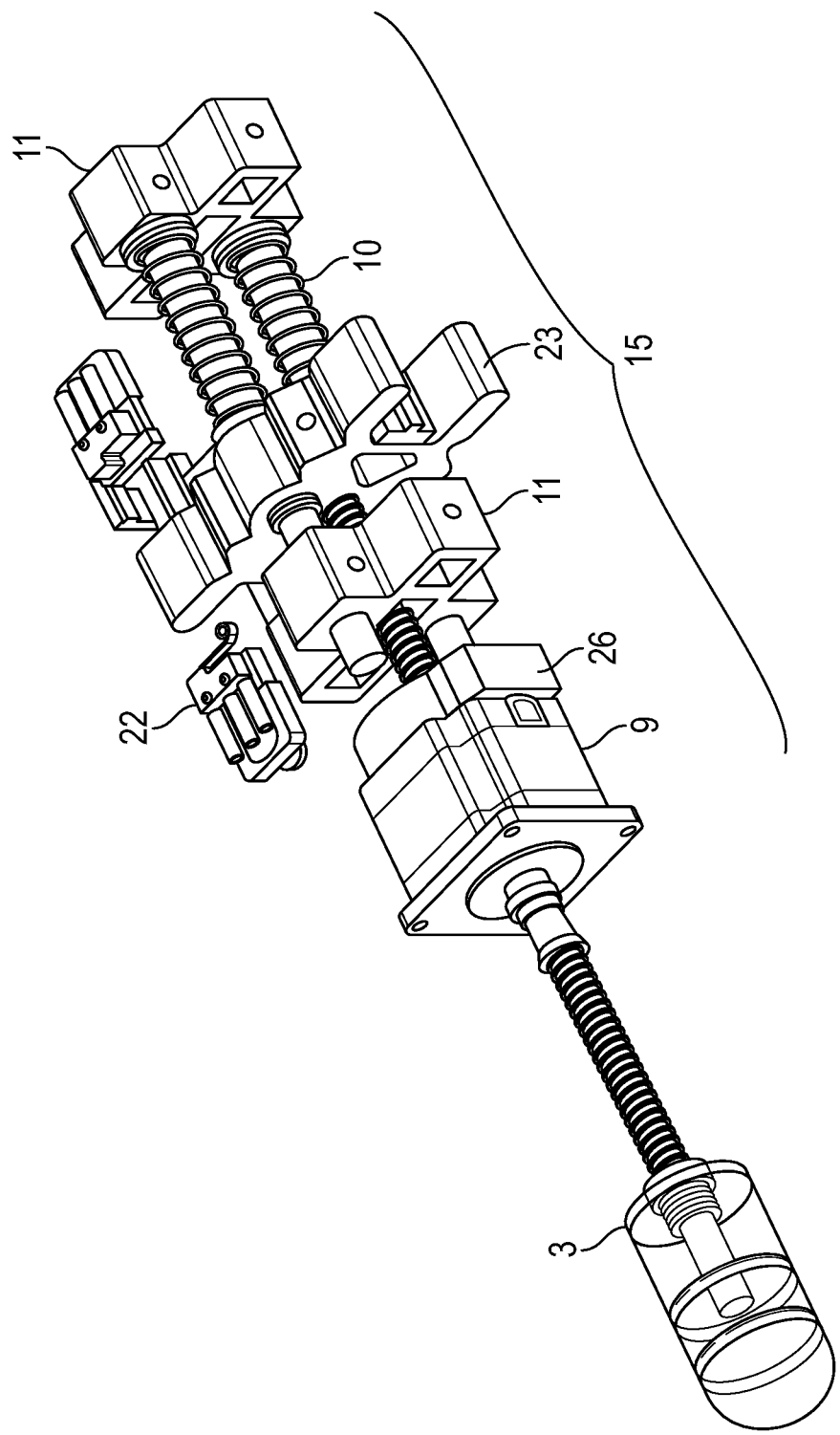
FIG. 13 provides an isolated view of the drivetrain with piston. This rendering illustrates the connected stepper motor with encoder, hard stops, limit switches, spring assembly, and motion guides.
Figure 14:
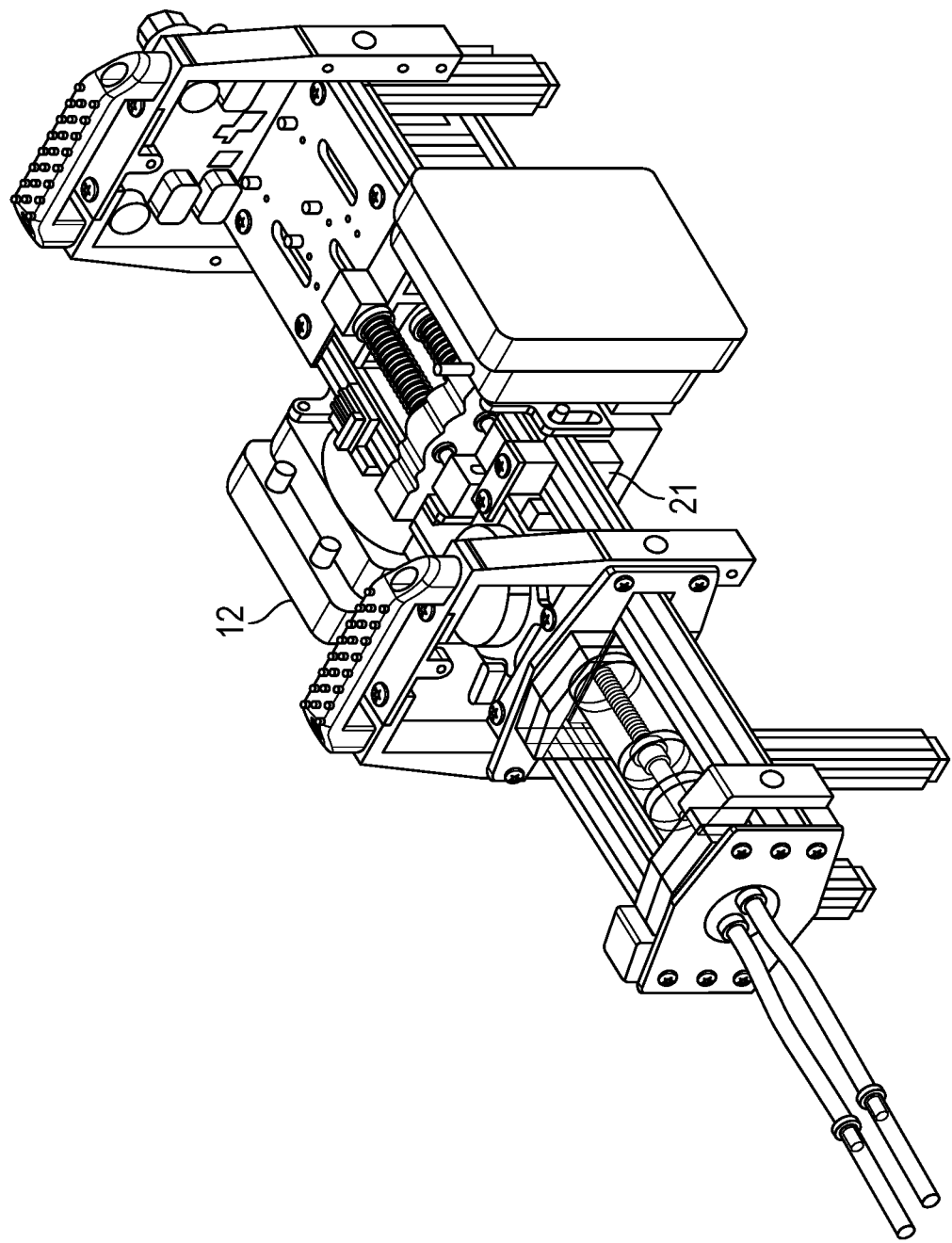
FIG. 14 provides a view of the design with the cooling system featured. The preferred embodiment of the subsystem is comprised of two cooling heads with attached radiators for heat dissipation.
Figure 15:
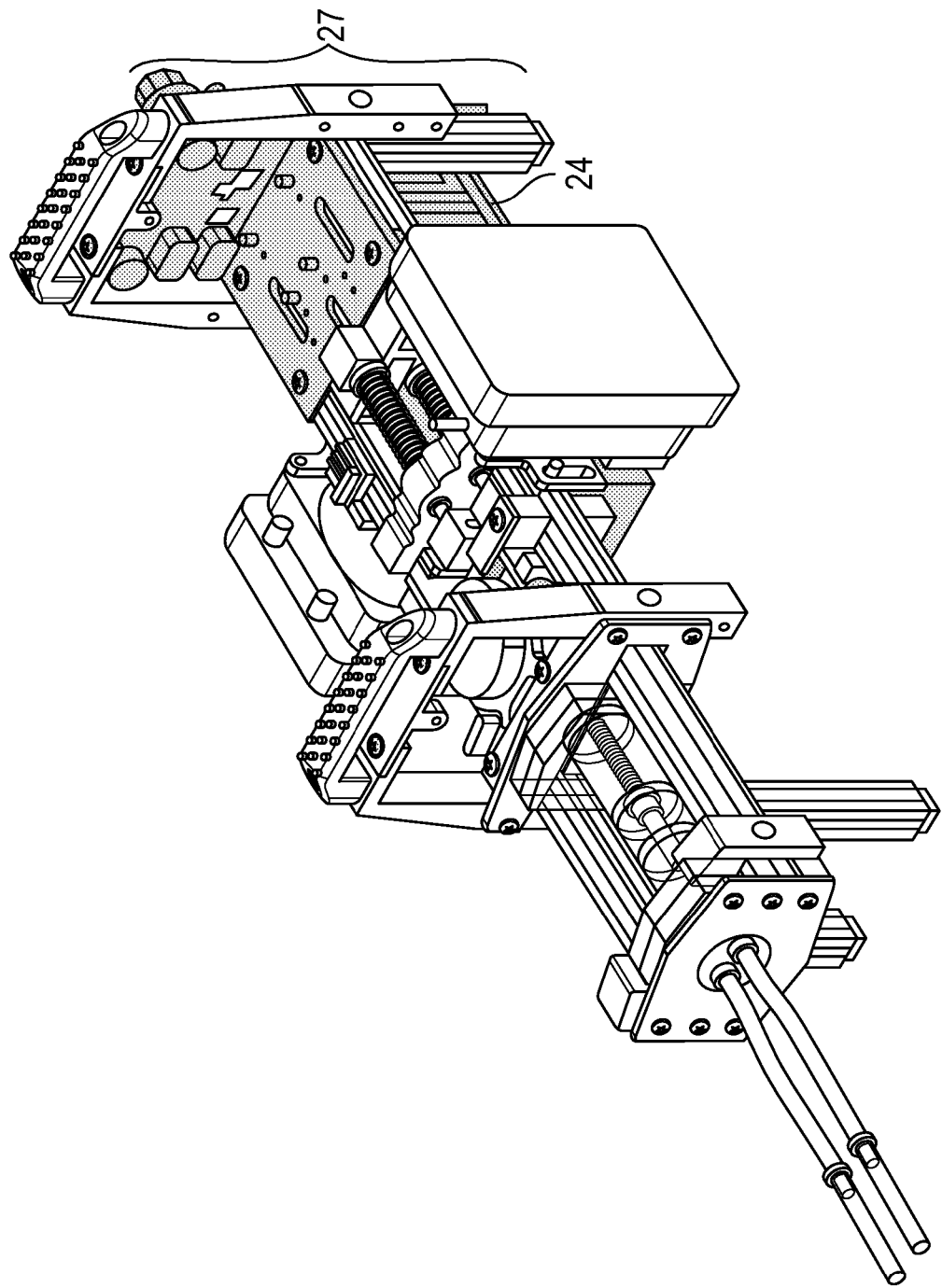
FIG. 15 provides a view of the design with the electronics and power supply subsystem shaded gray. The control boards are not included in this rendering. There are components not clearly visible in this rendering that are located under the power train assembly; notably, the motor power supply and electronics power supply.
Figure 16:
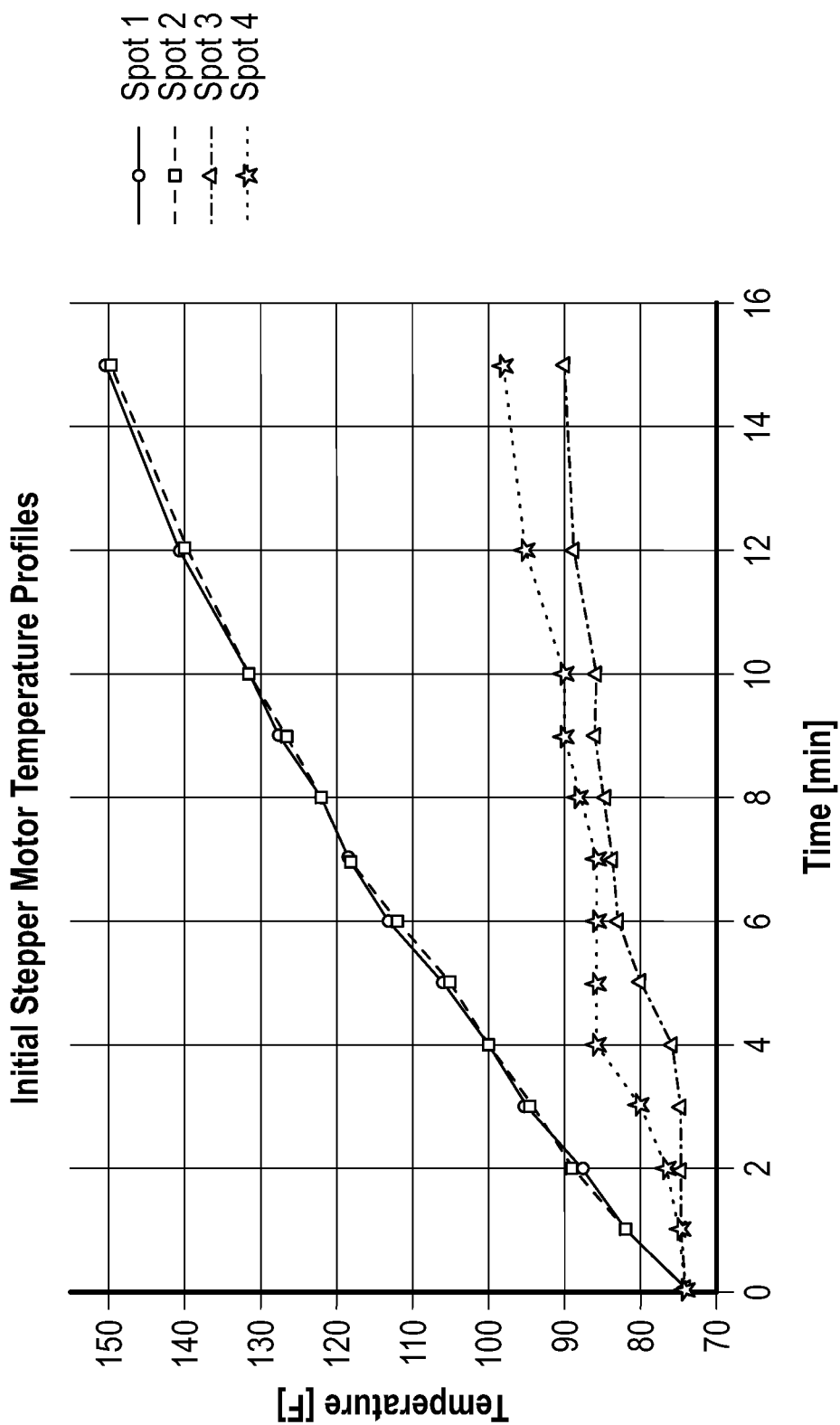
FIG. 16 provides the temperature profile of the pump in operation. Spot 1 is the side face of the drive unit pointing upward when mounted in the pump. Spot 2 is the back face of the drive that points towards the rear of the pump. Spot 3 and Spot 4 are the back and front of the leadscrew closest to the drive unit, respectively.
Figure 17:
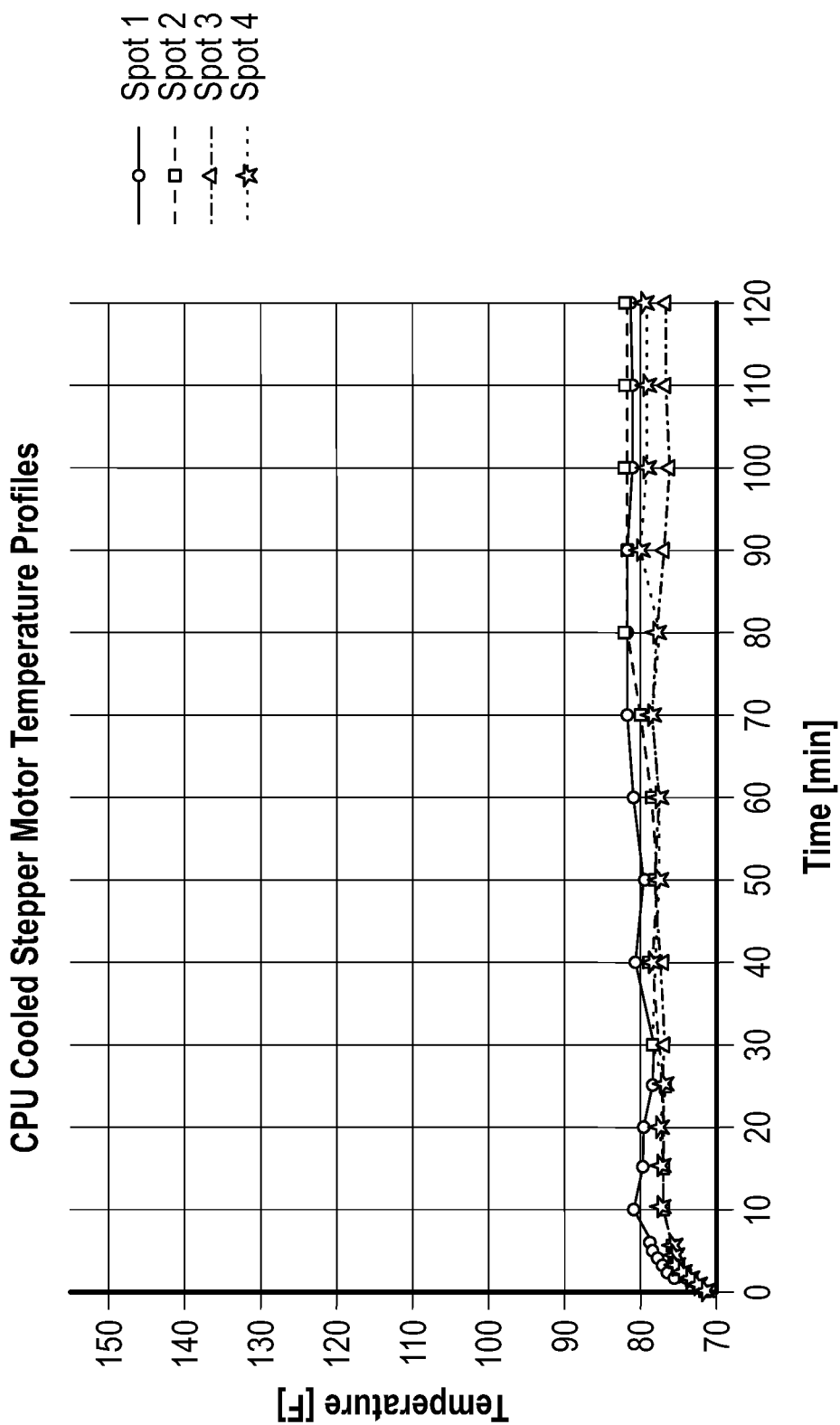
FIG. 17 provides the results of the liquid cooling implementation. The temperatures are well within the limit of safe operation for the drive and are low enough not to detrimentally affect the lubricants in the system. Spot 1 is the side face of the drive unit pointing upward when mounted in the pump. Spot 2 is the back face of the drive that points towards the rear of the pump. Spot 3 and Spot 4 are the back and front of the leadscrew closest to the drive unit, respectively.

The outlet fluidic connection of the return line 6 in FIG. 12 could be configured with pressure sensing hardware to detect pressure waves in the interfaced hydraulic system. This could be used as an additional input to trigger logic.

Operation of the pump could deliver fluidic agent that has an intended function within the interfaced system, that is synergized by the pressure or flow wave propagation in that destination flow. Operational settings of stroke volume, rate of delivery, and timing with the interfaced flow system could be parameters that relate to the functional performance of that fluidic agent.

Certain embodiments as described herein may include, but are not limited to the following components, as seen in the drawings:

1—Mounting plate
2—Pump head system
3—Piston
4—Frame system
5—Feed line
6—Return line
8—High flow check valve
9—Linear stepper motor
10—Spring system
11—Hard stop
12—Cooling subsystem
14—Acrylic pump casing
15—Actuator
16—Barb adapter
17—BNC connector
18—Continuously variable potentiometer
19—Control dial
20—Drive train system
21—Electronics power supply
22—Limit switch
23—Motion guide
24—Motion drive power supply
25—Pump casing component
26—Quadrature encoder
27—Electronics system The subject matter of the present invention is described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies. Although the terms "step" and/or "block" or "module" etc. might be used herein to connote different components of methods or systems employed, the terms should not be interpreted as implying any particular order among or between various steps herein disclosed unless and except when the order of individual steps is explicitly described.

Furthermore, the described features, structures, or characteristics may be combined in any suitable manner in one or more embodiments. Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

Moreover, the terms "substantially" or "approximately" as used herein may be applied to modify any quantitative representation that could permissibly vary without resulting in a change to the basic function to which it is related.

I claim:

1. A biocompatible positive displacement pump that triggers with the beating of a mammalian heart comprising:
   (a) a frame system;
   (b) a pump unit, comprising:
      (i) a pump head system;
      (ii) a pump casing component; and
      (iii) a drive train system, comprising a motor drive power supply;
   (c) an electronics system, comprising:
      (i) an electronics power supply;
      (ii) a microcontroller, comprising an operating code, which comprises:
         (1) an electrocardiogram (ECG) trigger subsystem;
         (2) a position encoder processing subsystem;
         (3) an operating controls subsystem;
         (4) an overwrite and error control subsystem;
         (5) a readback processing subsystem; and
         (6) programming to operate the pump;
      (iii) an interface board;
      (iv) a sensor shield;
      (v) an ECG signal condition board;
      (vi) a motion controller;
      (vii) at least one limit switch;
      (viii) an actuator;
      (ix) a quadrature encoder; and
      (x) at least one user control;
      wherein the microcontroller is connected to the interface board, the sensor shield, the ECG signal conditioning board, and the motion controller; wherein the interface board provides as least one output signal from the microcontroller to at least one Bayonet Neill-Concelman (BNC) connector;
      wherein the sensor shield is connected to the at least one user control, the at least one limit switch, and the quadrature encoder;
      wherein the ECG signal conditioning shield connects to an ECG wiring harness; and
      wherein the pump is operated using the at least one user control;
   wherein the frame system provides a mounting point for the pump head and electronics system; and
   wherein the electronics system is operatively connected to the pump unit.

2. A biocompatible positive displacement pump that triggers with the beating of a mammalian heart comprising:
   (a) a frame system;
   (b) a pump unit, comprising:
      (i) a pump head system;
      (ii) a pump casing component; and
      (iii) a drive train system, comprising a motor drive power supply;
   (c) an electronics system, comprising:
      (i) an electronics power supply;
      (ii) a microcontroller, comprising an operating code, which comprises programming to operate the pump and an operating control subsystem, wherein the operating controls subsystem comprises:
         (1) an action to motor;
         (2) an operating states table; and
         (3) a subsystem governs actuation motion;
      (iii) an interface board;
      (iv) a sensor shield;
      (v) an electrocardiogram (ECG) signal condition board;
      (vi) a motion controller;
      (vii) at least one limit switch;
      (viii) an actuator;
      (ix) a quadrature encoder; and
      (x) at least one user control;
      wherein the microcontroller is connected to the interface board, the sensor shield, the ECG signal conditioning board, and the motion controller; wherein the interface board provides as least one output signal from the microcontroller to at least one Bayonet Neill-Concelman (BNC) connector;
      wherein the sensor shield is connected to the at least one user control, the at least one limit switch, and the quadrature encoder;
      wherein the ECG signal conditioning shield connects to an ECG wiring harness; and
      wherein the pump is operated using the at least one user control;
   wherein the frame system provides a mounting point for the pump head and electronics system; and
   wherein the electronics system is operatively connected to the pump unit.

3. A biocompatible positive displacement pump that triggers with the beating of a mammalian heart comprising:
   (a) a frame system;
   (b) a pump unit, comprising:
      (i) a pump head system;
      (ii) a pump casing component; and
      (iii) a drive train system, comprising a motor drive power supply;
   (c) an electronics system, comprising:
      (i) an electronics power supply;
      (ii) a microcontroller, comprising an operating code comprising programming to operate the pump, and wherein the operating code is configured to match the pump head system's geometry;
      (iii) an interface board;
      (iv) a sensor shield;
      (v) an electrocardiogram (ECG) signal condition board;
      (vi) a motion controller;
      (vii) at least one limit switch;
      (viii) an actuator;
      (ix) a quadrature encoder; and
      (x) at least one user control;
      wherein the microcontroller is connected to the interface board, the sensor shield, the ECG signal conditioning board, and the motion controller; wherein the interface board provides as least one output signal from the microcontroller to at least one Bayonet Neill-Concelman (BNC) connector;
      wherein the sensor shield is connected to the at least one user control, the at least one limit switch, and the quadrature encoder;
      wherein the ECG signal conditioning shield connects to an ECG wiring harness; and
      wherein the pump is operated using the at least one user control;
   wherein the frame system provides a mounting point for the pump head and electronics system; and
   wherein the electronics system is operatively connected to the pump unit.

4. A biocompatible positive displacement pump that triggers with the beating of a mammalian heart comprising:
(a) a frame system;
(b) a pump unit, comprising:
  (i) a pump head system;
  (ii) a pump casing component; and
  (iii) a drive train system, comprising a motor drive power supply;
(c) an electronics system, comprising:
  (i) an electronics power supply;
  (ii) a microcontroller, comprising an operating code comprising programming to operate the pump, comprising:
    (1) an electrocardiogram (ECG) trigger subsystem;
    (2) a position encoder processing subsystem;
    (3) an operating controls subsystem, comprising:
      a. an action to motor;
      b. an operating states table, comprising:
        1. a prime state;
        2. a pause/idle state;
        3. a pump on trigger state; and
        4. a pump without trigger state;
    (iii)c. a subsystem governs actuation motion;
    (4) an overwrite and error control subsystem; and
    (5) a readback processing subsystem
  (iii) an interface board;
  (iv) a sensor shield;
  (v) an ECG signal condition board;
  (vi) a motion controller;
  (vii) at least one limit switch;
  (viii) an actuator;
  (ix) a quadrature encoder; and
  (x) at least one user control;
  wherein the microcontroller is connected to the interface board, the sensor shield, the ECG signal conditioning board, and the motion controller; wherein the interface board provides as least one output signal from the microcontroller to at least one Bayonet Neill-Concelman (BNC) connector;
  wherein the sensor shield is connected to the at least one user control, the at least one limit switch, and the quadrature encoder;
  wherein the ECG signal conditioning shield connects to an ECG wiring harness; and
  wherein the pump is operated using the at least one user control;
wherein the frame system provides a mounting point for the pump head and electronics system; and
wherein the electronics system is operatively connected to the pump unit.

* * * * *